United States Patent
Ivory et al.

(10) Patent No.: US 6,277,258 B1
(45) Date of Patent: Aug. 21, 2001

(54) DEVICE AND METHOD FOR FOCUSING SOLUTES IN AN ELECTRIC FIELD GRADIENT

(75) Inventors: Cornelius F. Ivory, Pullman, WA (US); Zheng Huang, Nantong (CN); Fred J. Schuetze, Pullman, WA (US)

(73) Assignee: Washington State University Research Foundation, Pullman, WA (US)

( * ) Notice: Subject to any disclaimer, the term of this patent is extended or adjusted under 35 U.S.C. 154(b) by 0 days.

(21) Appl. No.: 09/306,645

(22) Filed: May 6, 1999

Related U.S. Application Data

(60) Provisional application No. 60/084,505, filed on May 6, 1998.

(51) Int. Cl.⁷ ........................ G01N 27/26; G01N 27/447
(52) U.S. Cl. ..................... 204/450; 204/465; 204/600; 204/615; 210/198.2; 210/656; 73/61.53
(58) Field of Search ..................... 204/450, 600, 204/465, 615, 547, 548, 550, 551, 643, 644, 647, 648; 210/656, 657, 658, 659, 198.2; 73/61.53, 61.54, 61.55, 61.56, 61.57, 61.58

(56) References Cited

U.S. PATENT DOCUMENTS

| 4,148,703 | 4/1979 | Trop et al. . |
| 4,732,656 | * 3/1988 | Hurd . |

OTHER PUBLICATIONS

W.S. Koegler et al, "Field Gradient Focusing: A Novel Method for Protein Separation", Journal of the American Chemical Society and American Institute of Chemical Engineers, 15 pages, 1996.*

Greenlee, R.D., et al., "Protein Focusing in a Conductivity Gradient," *Biotechnology Progress,* vol. 14, No. 2, 1998, pp. 300–309.

Ivory, C.F., "The Prospects for Large–Scale Electrophoresis," *Separation and Purification Methods,* vols. 8 and 9, 1988, pp. 875–912.

Ivory, C.F., et al., Continuous Counteracting Chromatographic Electrophoresis, *Biotechnology Progress,* vol. 6, 1990, 12 pages.

Koegler, W.S., "Field Gradient Focusing: A Novel Method for Protein Separation," *Journal of the American Chemical Society and American Institute of Chemical Engineers,* 1996, 15 pages.

(List continued on next page.)

*Primary Examiner*—Jill Warden
*Assistant Examiner*—John S. Starsiak, Jr.
(74) *Attorney, Agent, or Firm*—Christensen O'Connor Johnson Kindness PLLC

(57) ABSTRACT

An electrophoretic device and method for focusing a charged solute is disclosed. The device includes a first chamber for receiving a fluid medium, the first chamber having an inlet for introducing a first liquid to the chamber and an outlet for exiting the first liquid from the chamber; a second chamber comprising an electrode array, the second chamber having an inlet for introducing a second liquid to the chamber and an outlet for exiting the second liquid from the chamber; and a porous material separating the first and second chambers. The device's electrode array includes a plurality of electrodes and generates an electric field gradient profile which can be dynamically controlled. In the method, a charged solute is introduced into a fluid medium followed by the application of a hydrodynamic force. Opposing the hydrodynamic force with an electric field gradient results in solute focusing in the fluid medium. The electric field gradient is generated by an electrode array by individually adjusting the electrode voltages.

44 Claims, 30 Drawing Sheets

OTHER PUBLICATIONS

Koegler, W.S., et al., "Focusing Proteins in an Electric Field Grandient," *Journal of Chromatography A,* 1996, pp. 229–236.

Locke, B.R., et al., "A Theoretical and Experimental Study of Counteracting Chromatographic Electrophoresis," *Separation and Purification Methods,* vol. 18, 1989, pp. 1–64.

O'Farrell, P.H., "Separation Techniques Based on the Opposition of Two Counteracting Forces to Produce a Dynamic Equilibrium," *Science,* vol. 227, Mar. 29, 1985, pp. 1586–1589.

* cited by examiner

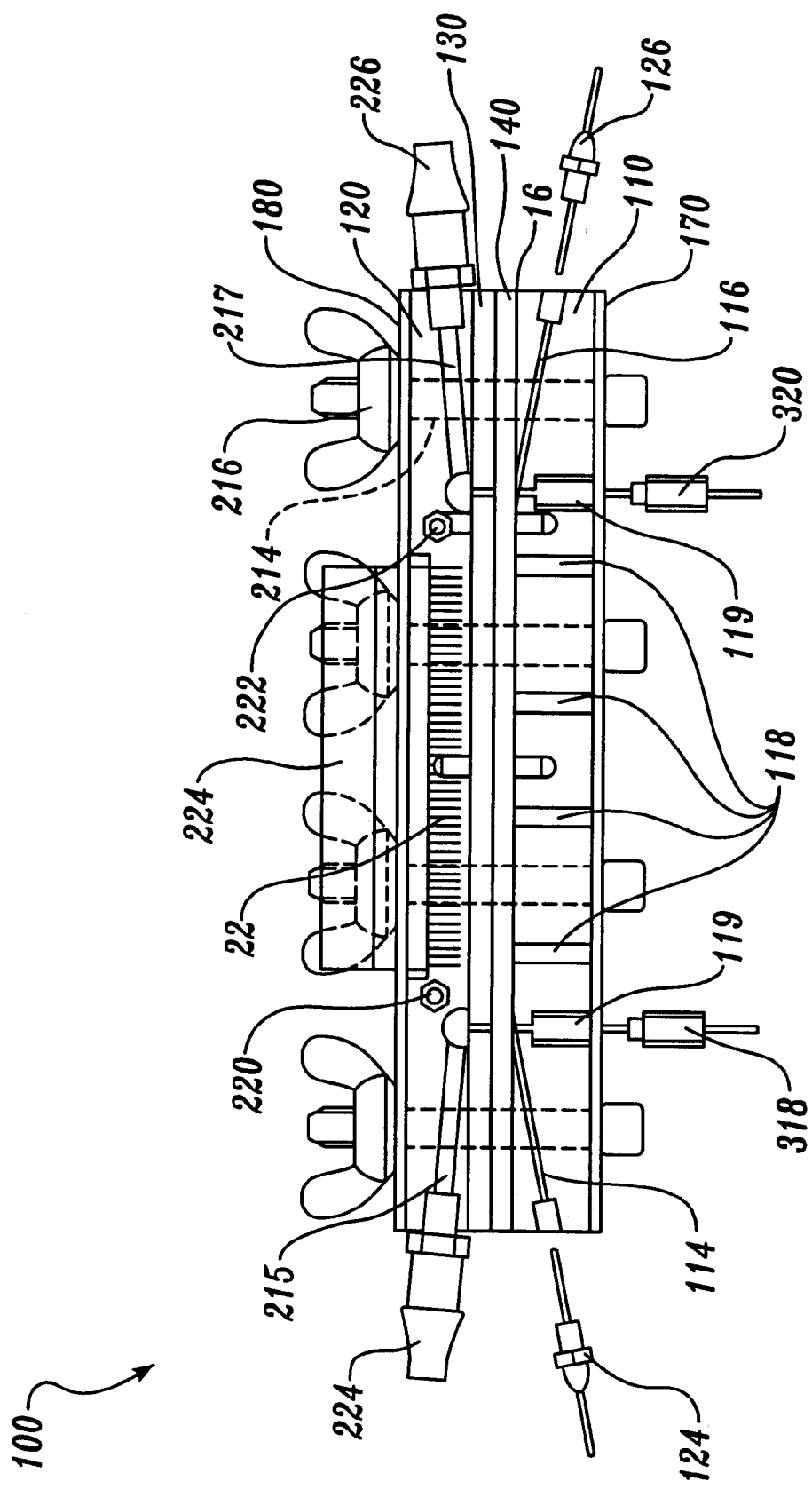

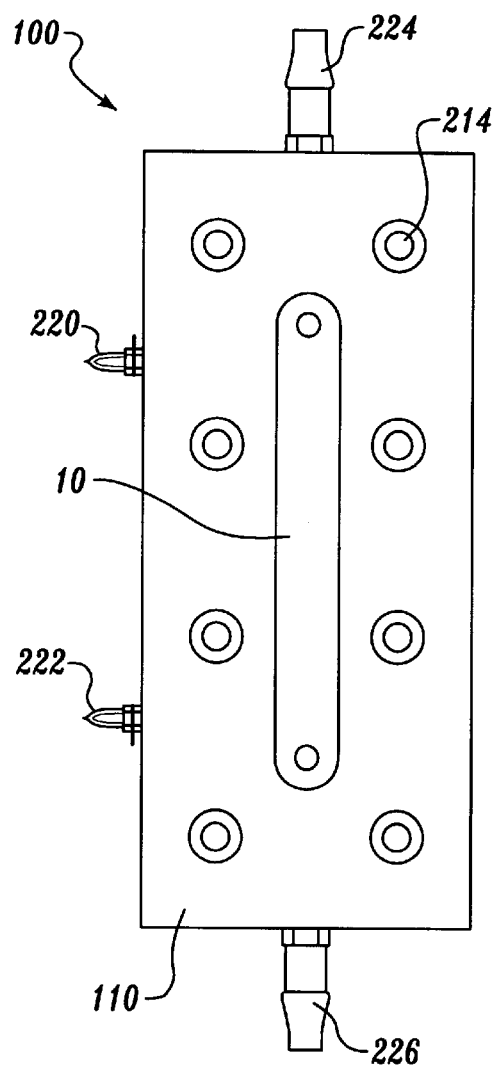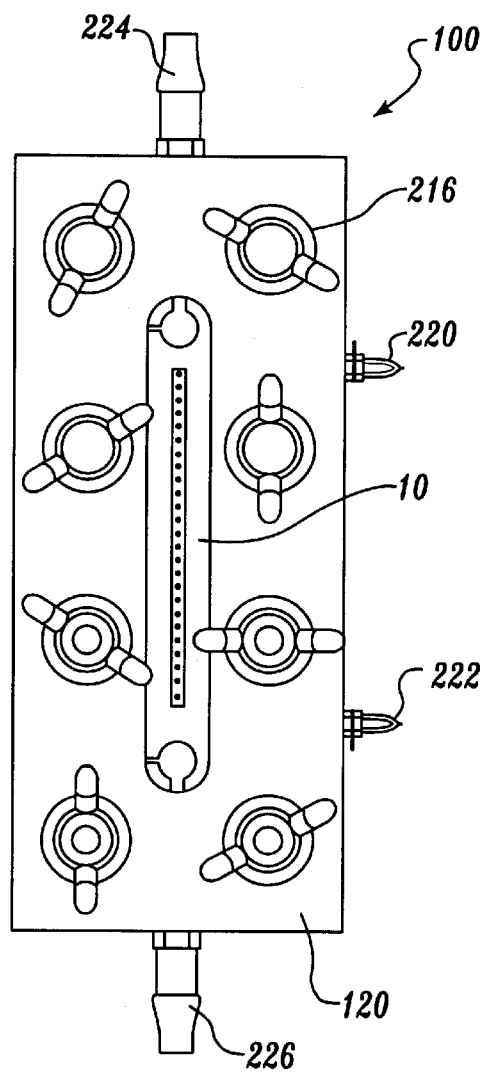
*Fig. 5A*  *Fig. 5B*

DEVICE AND METHOD FOR FOCUSING SOLUTES IN AN ELECTRIC FIELD GRADIENT

CROSS-REFERENCE TO RELATED APPLICATION

The present application claims the benefit under 35 U.S.C. 119(e) of the priority of the filing date of copending U.S. provisional application Serial No. 60/084,505, filed May 6, 1998, which is incorporated herein by reference.

FIELD OF THE INVENTION

The present invention relates to an electrophoretic device and method and, more particularly to an electrophoretic device and method that establishes and maintains an electric field gradient using an electrode array in which the electrode voltage is individually controlled.

BACKGROUND OF THE INVENTION

Electrophoresis is a gentle, inexpensive method of separating molecules based on their movement in an electric field. Electrophoresis can be carried out in free solution, e.g., an open capillary, slit or annulus, or with the aid of a support medium, such as a gel, polymer solution, or granular packing. Electrophoresis requires a buffered electrolyte to maintain the required pH and provide sufficient conductivity to allow the passage of current.

More than a decade ago, O'Farrell described a method known as counteracting chromatographic electrophoresis (CACE) in which proteins could be focused at the interface between two different gel filtration media packed into the upper and lower halves of an electrochromatography column. *Science* 1985, 227, 1586–1588. The results were soon replicated by others who found that at least one protein, ferritin, could be concentrated beyond 100 mg/mL. *Sep. Sci. Technol.* 1988, 23, 875; *Sep. Purif: Methods* 1989, 18, 1. This remarkable feat was tempered by the finding that his approach worked poorly with protein mixtures and would be difficult to scale up. *Biotechnol. Prog.* 1990, 6, 21. Nevertheless, O'Farrell had found a way to focus proteins in an electric field that did not require the use of a pH gradient.

CACE is only one member of a family of electrophoretic focusing techniques which can be described by the simple flux equation, $$N_{p,x} = -D_p \frac{dc_p}{dx} + \left( \langle u_{p,x} \rangle + z_p \omega_p \frac{I_x}{\sigma} \right) c_p = 0 \qquad (1)$$

where $N_{p,x}$, the molar flux of protein along the x-axis, is set equal to zero for stationary, focused protein bands. Eq.(1) is composed of a dispersive term, a convective term and an electrophoretic term where c is the protein concentration, $D_p$ is a diffusion or dispersion coefficient, $\langle u_{p,x} \rangle$ is the apparent chromatographic protein velocity along the x-axis, $z_p$ is the protein charge, $\omega_p$ is the protein mobility, $I_x$ is the current density and $\sigma$ is the electrical conductivity. In order for proteins to focus it is necessary that at least one of the terms in parentheses vary so that their sum (1) forms a gradient in which (2) vanishes at a single point in the chamber. Focusing occurs at the point in the chamber where the gradient vanishes.

Setting the sum of the terms in parentheses in eq.(1) equal to zero, it is seen that focusing may be accomplished in at least five different ways: (1) in a pH gradient with $u_p=0$, proteins will focus at the point where the net charge on the protein vanishes, i.e., $z_p=0$, as is the case with isoelectric focusing (IEF); (2) in a gradient in $u_{p,x}$ with $z_p$, I and $\sigma$ held constant, which corresponds to CACE; (3) in a gradient in $\omega_p$ with $u_{p,x}$ $z_p$, I and $\sigma$ constant, e.g., focusing a protein in a urea gradient, a technique which is still untested. With $u_p$ held constant there are still two ways left to focus proteins: by forming gradients in I or $\sigma$, both of which generate gradients in the electric field.

Recently, Koegler and Ivory demonstrated that charged proteins could be separated and focused using an electric field gradient in an electrochromatography column. *J Chromatogr.*, A 1996, 229, 229–236. A fluted cooling jacket was used to form a linear gradient in the electric field which drove the proteins against a constant flow of buffer in a packed dialysis tube. This approach was slow and cumbersome and gave mediocre results, but it successfully illustrated an alternative focusing technique known as electric field gradient focusing (EFGF).

Next, Greenlee and Ivory showed that proteins would focus in the electric field gradient formed by an axial conductivity gradient and opposed by a constant flow of buffer. *Biotechnol Prog.* 1998, 14, 300–309. Greenlee's apparatus was far simpler to build and operate than was Koegler's. The device was also surprisingly fast when run in free solution, reaching equilibrium in less than 10 min., and gave unexpectedly good results when filled with a 40-$\mu$m size exclusion (SEC) packing.

Focusing can also be achieved by opposing a constant convective velocity with a gradient in the electrophoretic velocity of the protein. This gradient can be created by varying the net charge on the protein (as in isoelectric focusing), by varying the cross-sectional area through which the electric current travels, as with electric field gradient focusing, or by varying the buffer conductivity.

Isoelectric focusing (IEF) is a gradient focusing method which varies the charge on a protein using a pH gradient. The convective velocity is usually set to zero while the net charge on the protein decreases as it approaches its isoelectric point (pI). The protein focuses at this point since its net charge, and therefore its electrophoretic velocity, both vanish at its pI.

Conventional IEF is usually performed in a support medium such as agarose or polyacrylamide gel. The pH gradient is formed by using a complex set of reagents known as carrier ampholytes which generate a stable, linear pH gradient under the influence of an applied electric field. Proteins migrate to the region where the ampholyte solution pH is equal to its own pI. In gels, detection of the focused bands involves a time consuming stain/destain procedure, and the ampholytes should be removed before the stain is applied. Established IEF protocols and a succinct history of its development are given by Righetti (1983).

Despite the advances in the electrophoretic methods and devices noted above, a need exists for electrophoretic methods and devices that can effectively separate charged solutes, such as protein mixtures, into their component solutes. The present invention seeks to fulfill these needs and provides further related advantages.

SUMMARY OF THE INVENTION

In one aspect, the present invention provides an electrophoretic device for focusing a charged solute. The device includes a first chamber for receiving a fluid medium, the first chamber having an inlet for introducing a first liquid to the chamber and an outlet for exiting the first liquid from the chamber; a second chamber comprising an electrode array, the second chamber having an inlet for introducing a second liquid to the chamber and an outlet for exiting the second liquid from the chamber; and a porous material separating the first and second chambers. In the device, the first and second chambers are in liquid communication when the chambers are filled with liquid and the first chamber is in electrical communication with the electrode array when the chambers are filled with a conductive liquid. The device's electrode array includes a plurality of electrodes arranged along the chamber length and each electrode is individually controlled. The electrode array generates an electric field gradient profile which can be dynamically controlled. The device is useful for focusing charged solutes and for separating mixtures of charged solutes.

In another aspect of the present invention, an electrophoretic method for focusing a charged solute is provided. In the method, a charged solute is applied to a fluid medium and then a hydrodynamic force is applied to the solute in the fluid medium. Opposing the hydrodynamic force with an electric field gradient results in solute focusing in the fluid medium. The electric field gradient is generated by an electrode array by individually adjusting the electrode voltages of each element of the array.

In accordance with the invention, the electronically generated field can take on arbitrary shapes including exponential profiles, steps, and even locally reversed gradients, for example, to elute proteins. The field shape can be monitored and maintained by computer and modified "on-the-fly" on a point-by-point basis, both spatially and temporally. During a run the operator can optimize the local properties of the field to tease proteins apart, sharpen an individual band, move a band to an offtake port or set up a moving gradient to elute one or more bands from the chamber. With online (e.g., optical or potentiometric) monitoring in place, the operator could be replaced by a computer programmed to detect focused peaks and automatically adjust the field shape to optimize the separation and, when necessary, offload products.

BRIEF DESCRIPTION OF THE DRAWINGS

The foregoing aspects and many of the attendant advantages of this invention will become more readily appreciated by reference to the following detailed description, when taken in conjunction with the accompanying drawings, wherein:

FIG. 4 is an elevation view of a representative device formed in accordance with the present invention;

FIGS. 5A and 5B are front and back plan views, respectively, of a representative device formed in accordance with the present invention;

DETAILED DESCRIPTION OF THE PREFERRED EMBODIMENT

Figure 1:
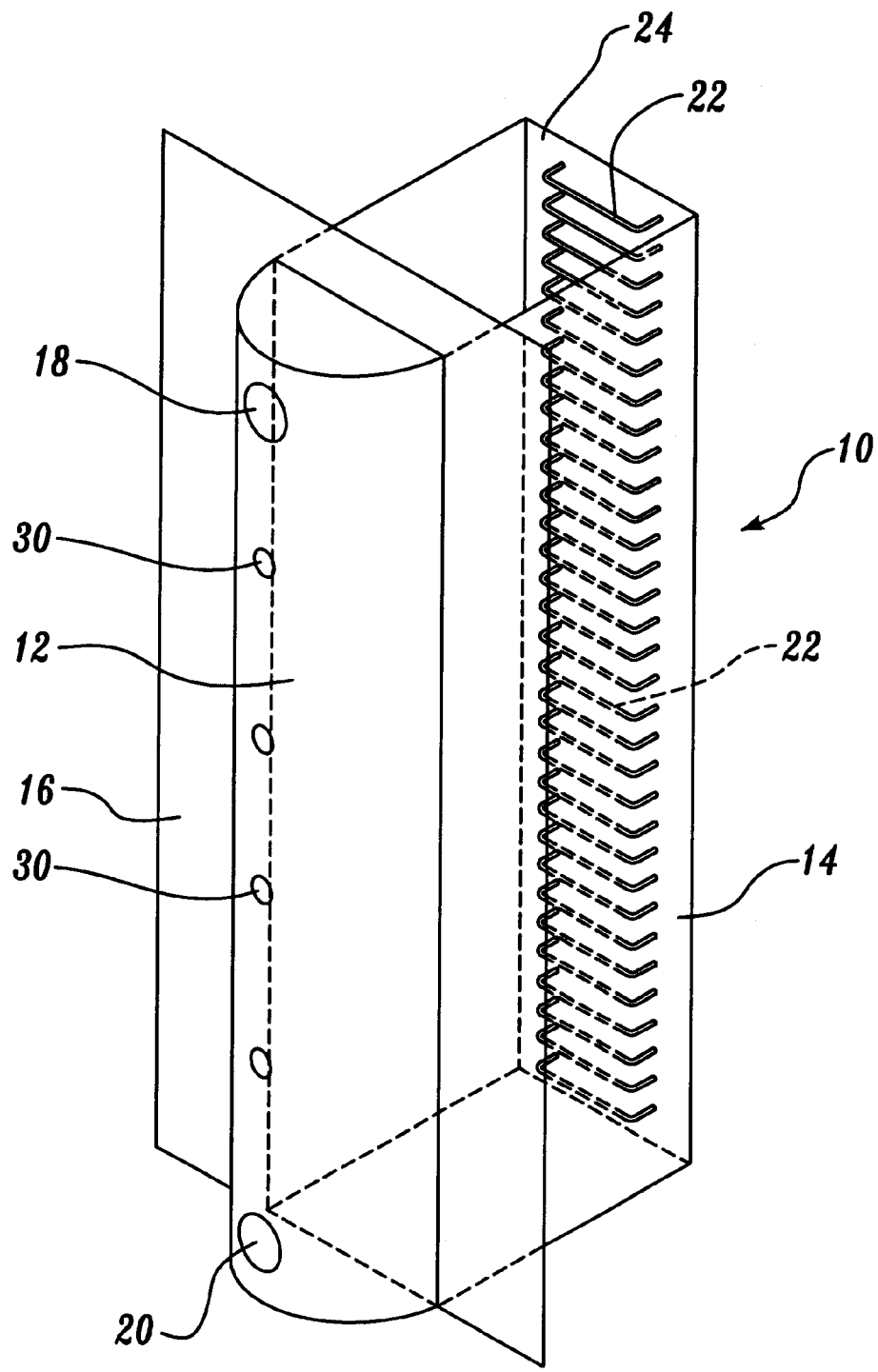
FIG. 1 is a schematic drawing of a representative device formed in accordance with the present invention.

The present invention provides an electrophoretic device and method in which a charged solute such as a protein can be simultaneously separated and concentrated by applying a first constant force (e.g., hydrodynamic force due to buffer flow) and opposed by a gradient in a second force (e.g., electric field). According to the invention, a constant hydrodynamic force is opposed by a gradient in the electric field which allows charged molecules to focus in order of their apparent electrophoretic mobilities. The electric field gradient is established and maintained using an array of electrodes whose voltages are individually monitored and adjusted by a computer-controlled circuit board. The computer-generated electric field gradient allows charged molecules to be focused without using a pH gradient. For proteins, because the proteins are not focused at their pIs, precipitates do not form, so focused concentrations in excess of 50 mg/mL are not unusual. In addition, because the field shape is dynamically controlled from the computer on a point-by-point basis, the field profile can be adjusted during a run to improve the resolution of components.

In one aspect, the present invention provides an electrophoretic device that :includes a focusing chamber having an electrode array. The focusing chamber is a divided chamber that includes a separation chamber and an electrode chamber separated by a porous material. Charged solute separation and focusing occurs in the separation chamber which includes a fluid medium. The electrode chamber includes an array of electrodes for generating a focusing electric field gradient. The separation chamber is in liquid and electrical communication with the electrode chamber through the porous material. The porous material retains solutes in the separation chamber and is permeable to certain solutes such that the electrode chamber and separation chambers are in liquid communication. Generally, an eluant is introduced into and flows through the separation chamber containing the charged solute. The eluant flow is opposed to the direction of electrophoretic migration of the solute. The electrode array in the electrode chamber renders the separation chamber an electrochromatography column.

The device can optionally include, in addition to the electrode array, an electrode pair. In this embodiment, the electrode's of the pair are positioned adjacent opposing ends of the electrode array.

As noted above, the focusing chamber includes an electrode array. As used herein, the term "electrode array" refers to a plurality of electrodes arranged so as to generate an electric field gradient in the separation chamber for focusing a charged solute according to its electrophoretic mobility. The electric field generated by the electrode array can be DC, AC, or otherwise modulated in time including asymmetric (out of phase) field modulation. The specific nature of the electrode (i.e., size and shape) is not critical. Suitable electrodes include pin-shaped and staple-shaped electrodes, among others. In one embodiment, the electrode array includes a linear array of electrodes (e.g., 50 electrodes arranged linearly) along an axis parallel to the direction of solute migration. In addition to arrays having electrodes arranged in line with even spacings from one to the next, suitable arrays also include arrays in which the electrodes are not in line and which are not separated by even spacings. Other configurations of electrodes include two-dimensional electrode arrays and are also within the scope of the invention. Two-dimensional arrays include arrays having rows and columns of electrodes. The focusing chamber can include more than one electrode array.

Each electrode of the array is individually controlled to provide an electric field gradient that is dynamically controlled (i.e., maintained and adjusted during the course of solute focusing and/or separation). Control can be manual from the device controller, manually from the device's associated computer, or automatically from the computer once the computer has received feedback from a monitor (e.g., optical monitor such as a video signal) following solute focusing. The controller can sense the electrode's voltage and reset its voltage to its initial setting.

The separation and electrode chambers are separated by a porous material such that the chambers are in liquid and electrical communication. Liquid communication refers to the ability of liquid to pass through the porous material while (1) desired solutes are retained in the separation chamber; (2) undesired contaminants can be dialyzed out of the separation chamber; and desired molecules can be dialyzed into the separation chamber. The porous material include materials that permit the liquid communication described above. Suitable porous materials include porous membranes such as dialysis membranes and ion exchange membranes.

The separation chamber includes a fluid medium. As used herein the term "fluid medium" refers to any fluid medium in which a charged solute can be focused. Suitable fluid media include a simple fluid (e.g., buffered water), complex fluid (e.g., a water, acetonitrile, methanol mixture), or polymer solution (e.g., linear polyacrylamide, polyvinyl alcohol, methyl cellulose solutions). The fluid medium can also include a chromatography support medium or packing. Suitable packings can be of any size or type provided that the solute being focused does not irreversibly bind to the packing. Packings can be porous or nonporous, pellicular or tentacle, glass, plastic, ceramic, any nonconductor or semiconductor. Other suitable packings include ion-exchange, affinity, reverse phase size exclusion, gel filtration, and hydrophobic interaction supports.

In operation, the device includes the flow of a first liquid through the separation chamber and the flow of a second liquid through the electrode chamber. Generally, the first liquid is an electrophoretic eluant (e.g., buffer solution) and the second liquid is a coolant. The first liquid can be the same as or different from the second liquid. During focusing and depending on the requirements of the particular separation, the composition of either the first and/or the second liquid can be changed to achieve the desired result. As noted above, liquid flow through the separation chamber opposes the direction of electrophoretic migration of the solute and can be driven by any one of a variety of forces including electric field, pressure, vacuum, or other motive force. In a preferred embodiment, the direction of liquid flow through the separation chamber is opposite that through the electrode chamber.

The device is useful in focusing and separating charged solutes. Charged solutes that can be focused include charged biological solutes such as proteins, peptides, oligonucleotides, polynucleotides, and mixtures of these can be advantageously focused in the device. Uncharged materials sorbed into charged carriers such as micelles and liposomes can also be focused with the device.

The device is useful in focusing, concentrating, and separating charged solutes. The focused solutes can be eluted from the device through one or more separation ports. Basically, the desired solute can be focused to a region of the chamber from which the solute can be eluted through a port. Solutes can be eluted from the separation chamber by electric field, pressure, vacuum, or other motive force.

The device can further include a monitoring feature which detects solute migration. Suitable solute detection includes optical and potentiometric methods. Integration of detection signal with software allows automation and computer optimization of solute loading, separation, and elution steps.

The device can be operated in a continuous mode in which solute for focusing and/or separation is continuously loaded into the separation chamber and focused to offtake ports where the solutes are continuously eluted. The continuous mode is in contrast to the batch mode in which the solute is loaded in its entirety and then focused. The device can be operated in either mode.

The device offers scale independent control. The device is useful in focusing solutes ranging in amount from micrograms to grams. As described below, the basic device, controller, software, monitoring, and circuitry permit the focusing of a wide range of amounts of solutes.

Figure 2:
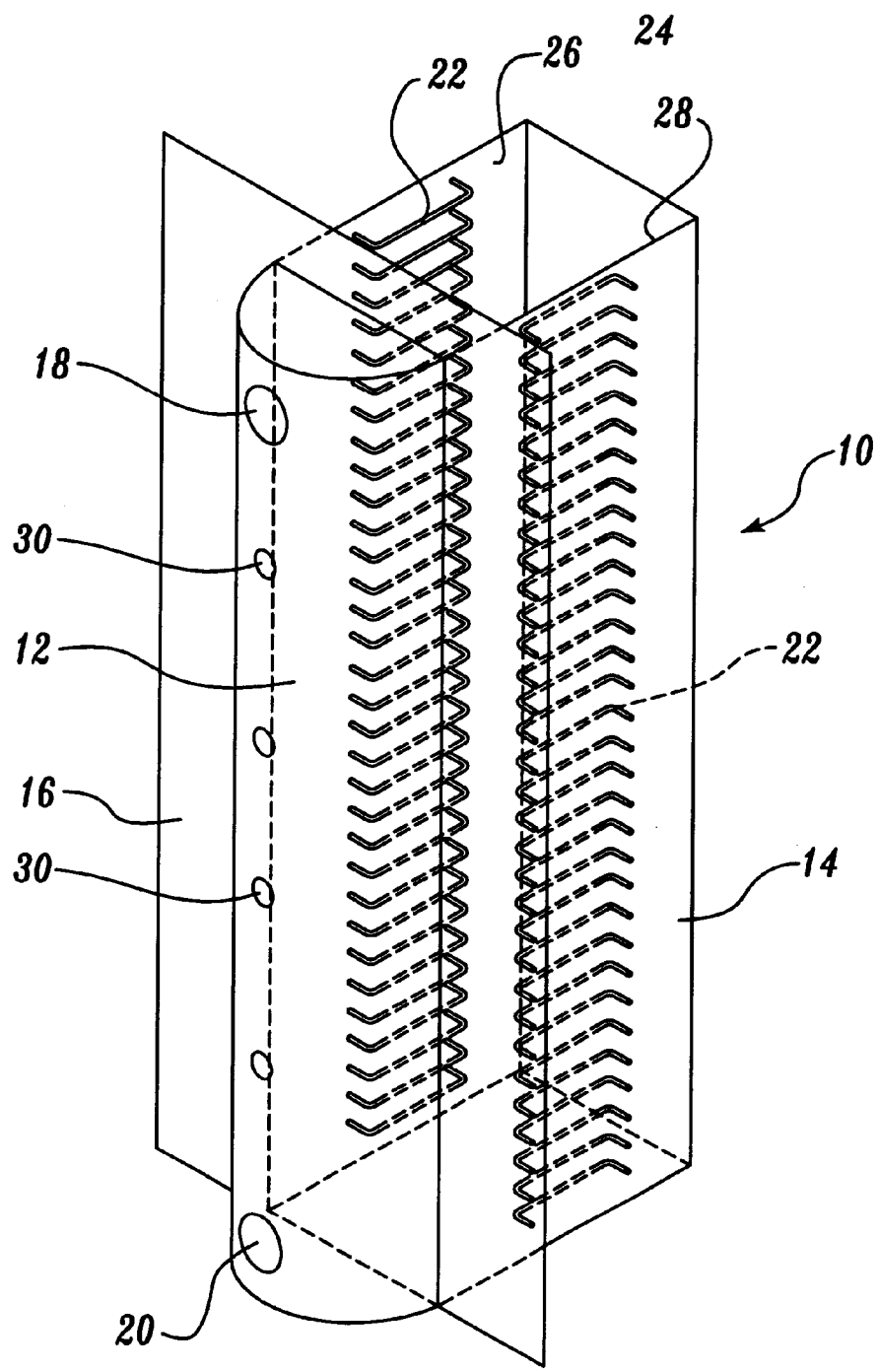
FIG. 2 is a schematic drawing of a representative device formed in accordance with the present invention.
Figure 3A:
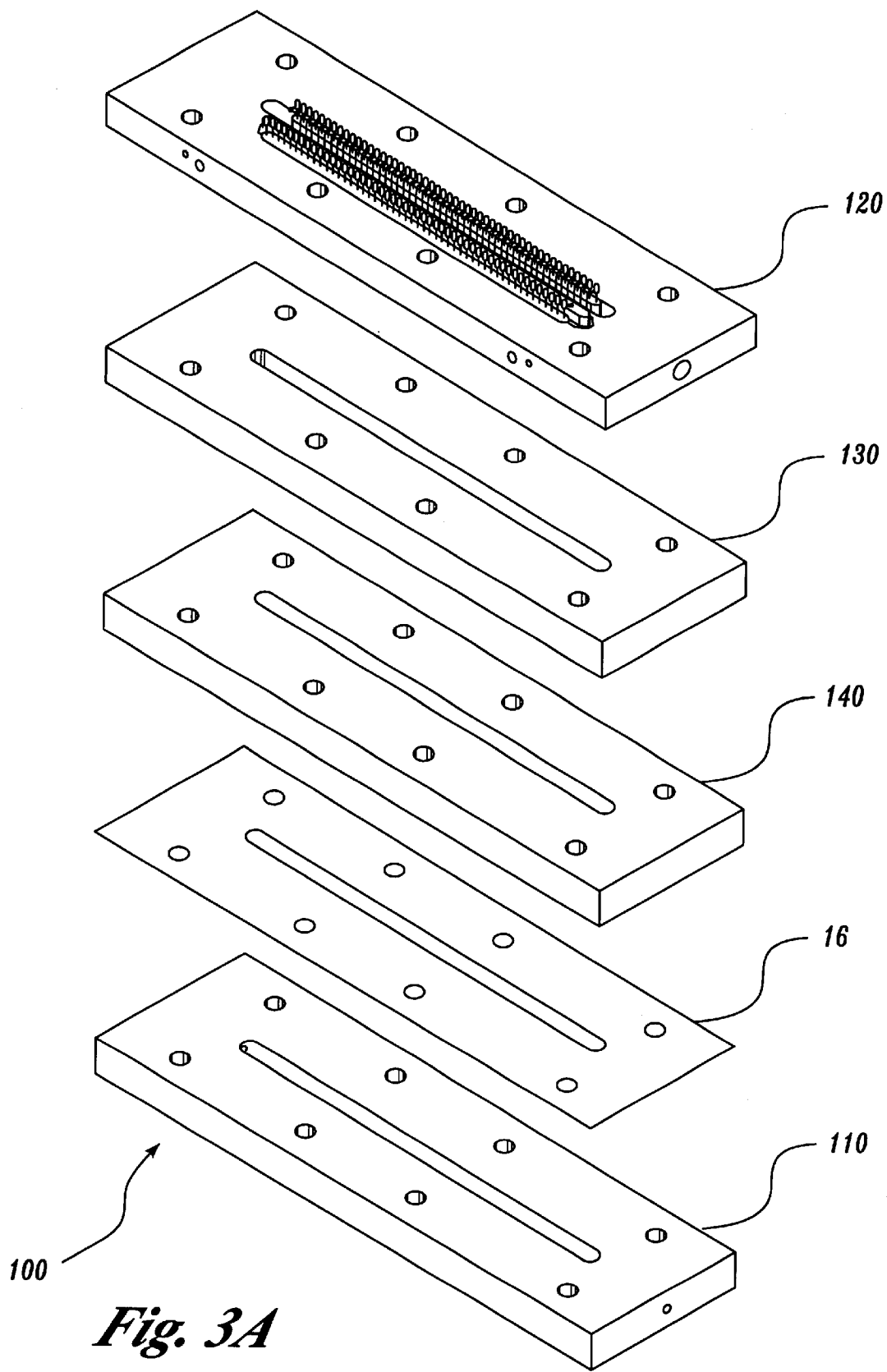
FIG. 3A is an exploded view of a representative device formed in accordance with the present invention.
Figure 3B:
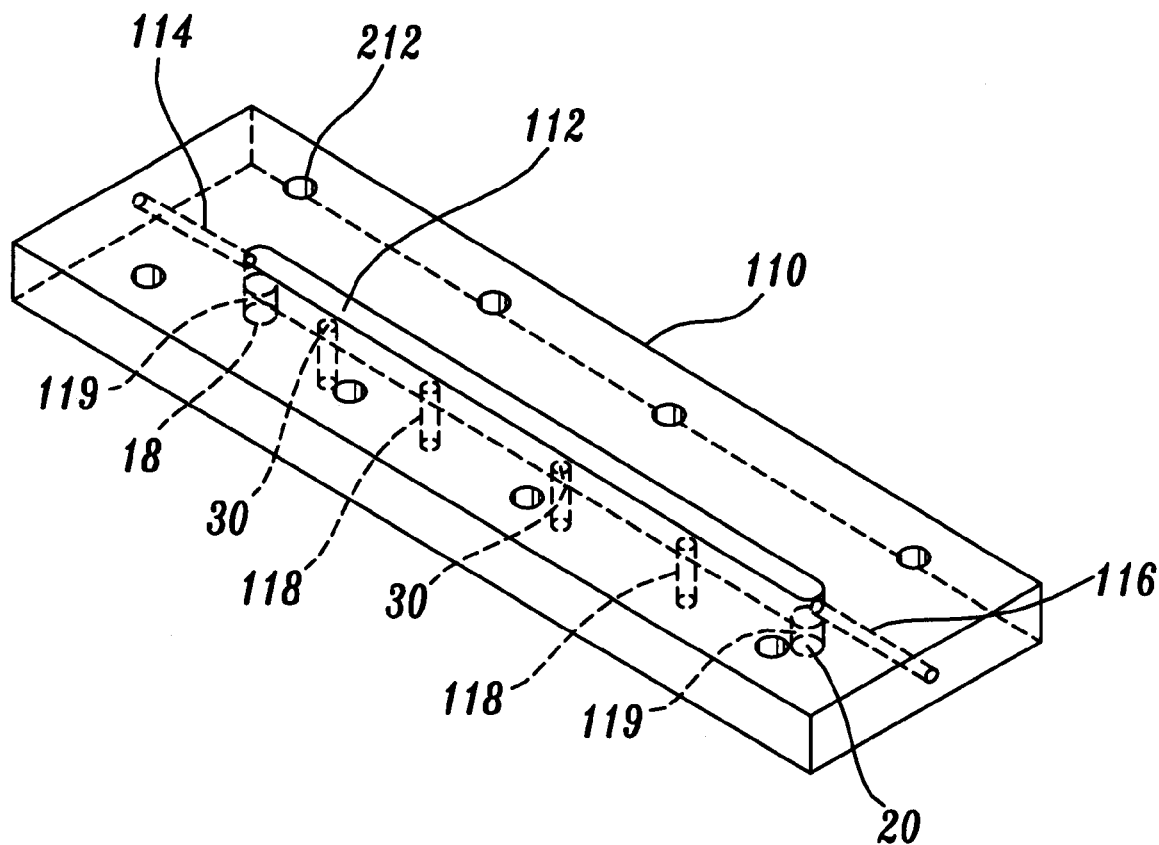
FIGS. 3B–3E are schematic drawings of the components illustrated in FIG. 3A.
Figure 3C:
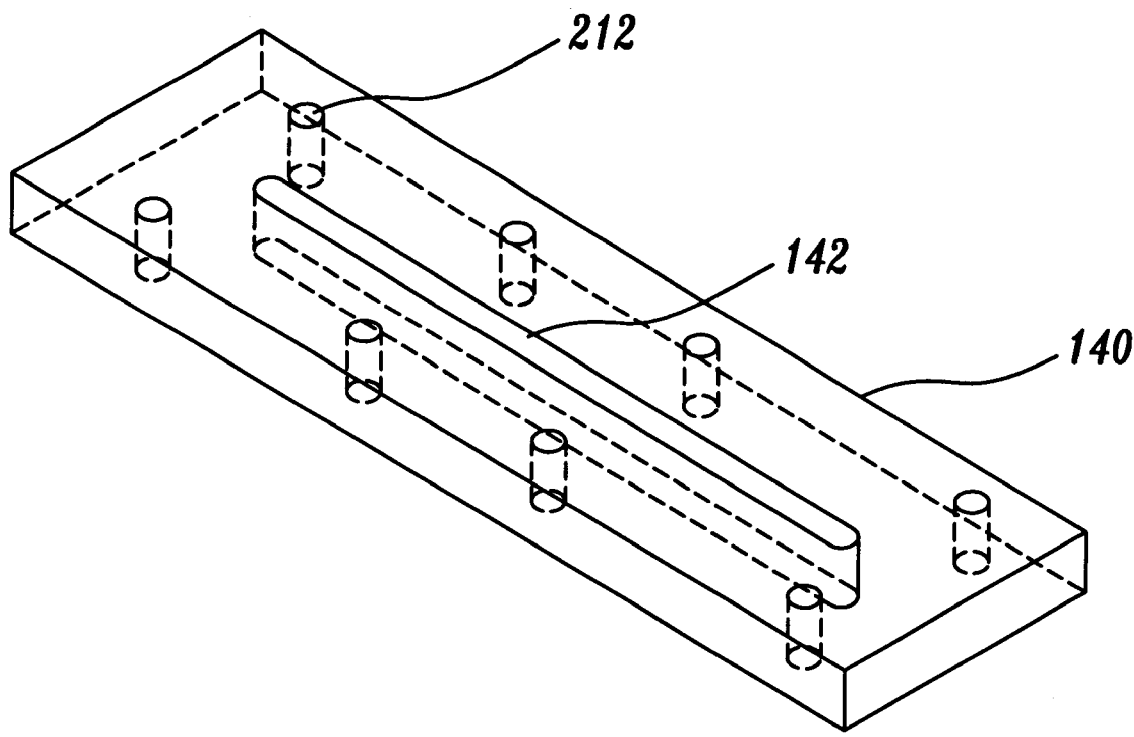
Figure 3D:
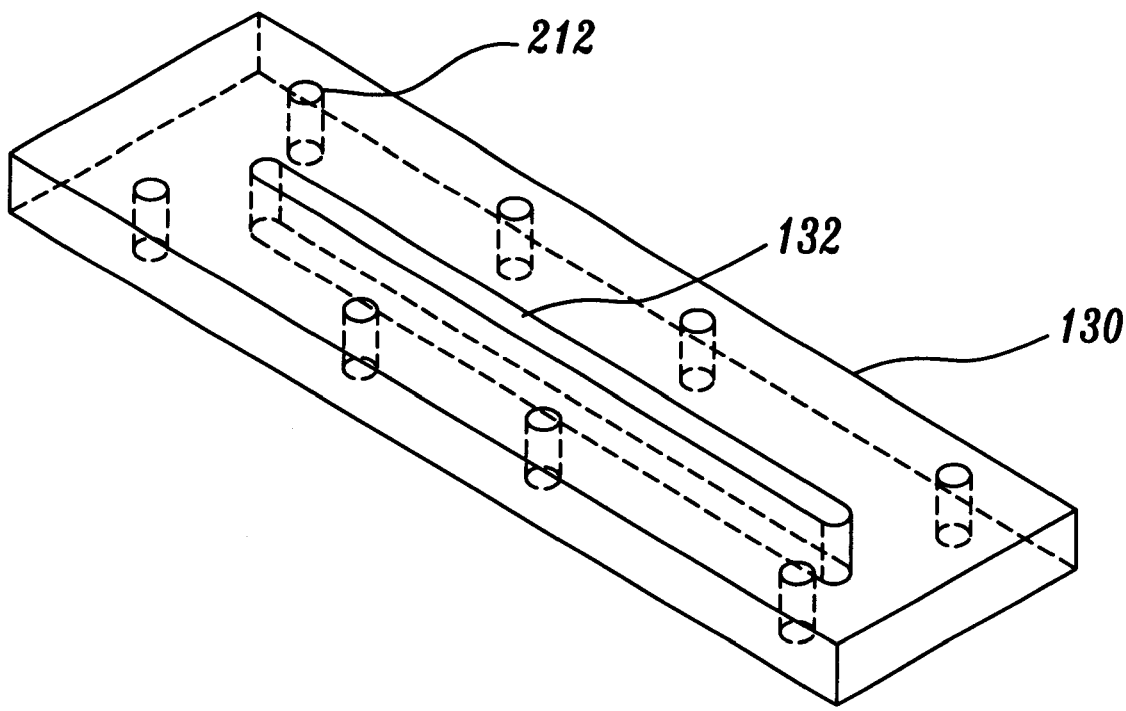
Figure 3E:
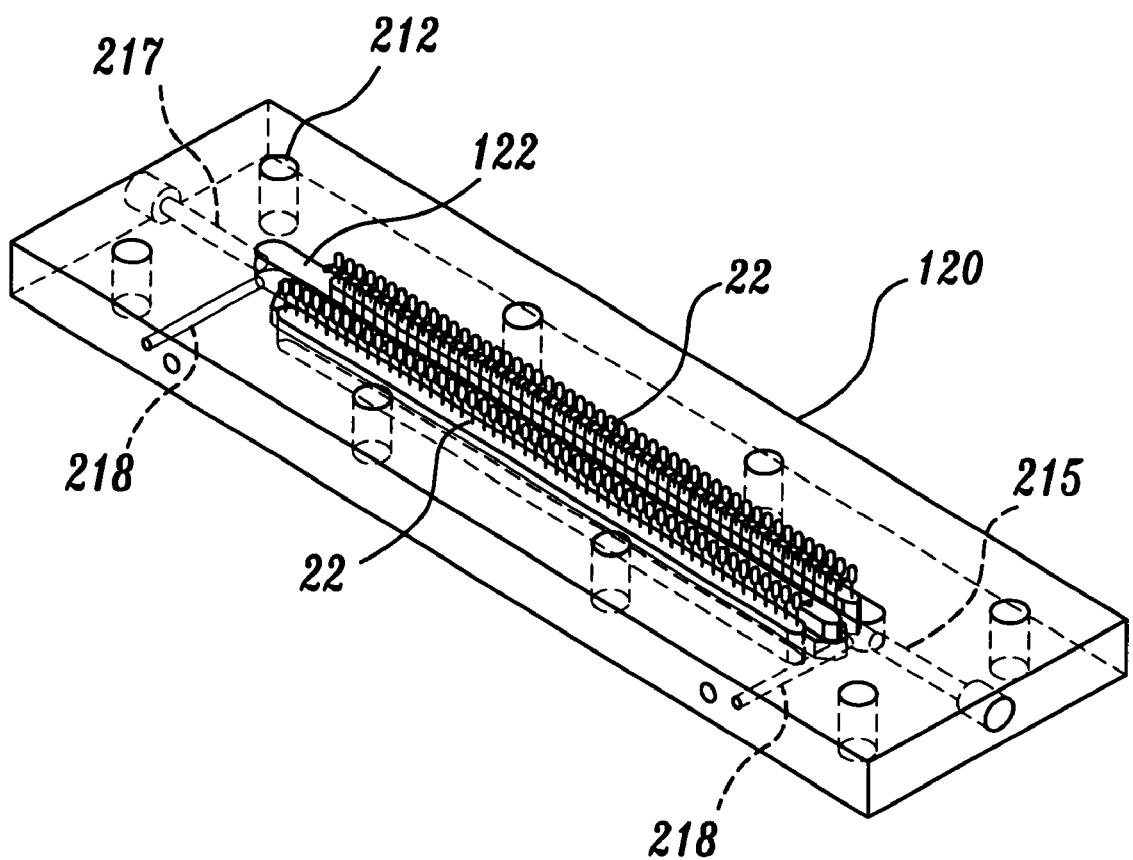

A representative focusing chamber formed in accordance with the present invention is shown schematically in FIG. 1. Referring to FIG. 1, focusing chamber 10 includes separation chamber 12 and electrode chamber 14 separated by porous member 16. Separation chamber 12 includes elution buffer inlet 18 and outlet 20. In operation, in one embodiment, elution buffer flows downward from inlet 18 through chamber 12 exiting outlet 20, and coolant buffer flows through electrode chamber 14, preferably upwardly. Electrode chamber 14 includes an array of electrodes 22. As shown in FIG. 1, the electrode array can be positioned on the electrode chamber surface 24 opposing separation chamber 12 and porous member 16. Alternatively, as shown in FIG. 2, the electrode chamber includes a pair of electrode arrays. Referring to FIG. 2, in this embodiment, the electrode array includes an electrode array positioned on electrode chamber surfaces 26 and 28 adjacent separation chamber 12 and porous member 16. Device 10 can further include one or more ports 30 for eluting solutes from the separation chamber.

A representative electrophoretic device formed in accordance with the present invention including a focusing chamber as described above is shown in FIGS. 3–6. FIG. 3 shows an exploded view of the device including front and rear portions. An elevation view of the device is shown in FIG. 4, and forward and rear plan views of the device as illustrated in FIGS. 5A and 5B, respectively. A cross-sectional view of a portion of a representative device illustrating the separation chamber, porous membrane, and electrode chamber is shown in FIG. 6.

A representative device including a focusing chamber is shown in FIG. 3. The embodiment illustrated in FIG. 3 includes side-by-side electrode arrays as shown in FIG. 2. Referring to FIG. 3, device 100 has basic components including first block 110 and second block 120 separated by intermediate sheets 130 and 140. Porous member 16 is intermediate block 110 and sheet 140. Blocks 110 and 120 and intermediate sheets 130 and 140 are formed from machinable materials. Preferably, blocks 110 and 120 and intermediate sheet 130 are formed from PLEXIGLAS and sheet 140 is formed from TEFLON. In one embodiment, each component includes a plurality of apertures 212 that are coincident with the apertures of the other components when the components are assembled. Apertures 212 receive bolts 214 (see FIG. 4) for securing the assembled components and assist in sealing the assembly. As shown in FIG. 4, the components are secured through tightening nuts 216 on bolts 214.

To form the focusing chamber, first block 110 and second block 120 include troughs 112 and 122, respectively. Trough 122 includes the electrode arrays, each array comprising a plurality of electrodes 22. Sheets 130 and 140 include apertures 132 and 142, respectively. When the components are assembled, troughs 112 and 122 and apertures 132 and 142 are coincident and form a portion of the focusing chamber 10. Intermediate sheet 140 and block 110 is porous member 16 which divides chamber 10 into separation chamber 12 and electrode chamber 14.

First block 110 includes conduits 114 and 116 which terminate in opposing ends of trough 112. Conduits 114 and 116 serve as inlet and outlet, respectively, for introducing fluid media (e.g., chromatography support material) to and removing the media from the separation chamber. First block 110 further includes channels 118 which terminate in trough 112, which provide for eluting focused solutes from the device through offtake ports 30 (see FIGS. 1 and 2). Channels 119 also terminate in trough 112 and provide for introducing charged solute and eluant to the separation chamber through inlet 18 and exiting eluant through outlet 20 (see FIGS. 1 and 2).

Second block 120 includes conduits 215 and 217, which terminate in opposing ends of trough 122. These conduits serve to introduce and exit liquid flow (e.g., coolant) through the electrode chamber. For embodiments of the device that include an electrode pair in addition to the electrode array, second block 120 further includes channels 218 which terminate in trough 122. Channels 218 receive electrodes 220 and 222, which like the electrode array, are in electrical communication with liquid in the electrode chamber when the device is in operation.

The assembled device is illustrated in FIGS. 4 and 5. Referring to FIG. 4, device 100 includes blocks 110 and 120 and sheets 130 and 140, and porous member 16. Conduits 114, 116, 215, and 217, noted above, are illustrated along with connecting devices 124, 126, 224, and 226, respectively, which serve to connect the focusing chamber with its respective supplies. Inlet connection device 318 and outlet connecting device 320 are illustrated and communicate with channels 119 and separation chamber inlet 18 and outlet 20, respectively. Connector 224 leads to the device's controller and provides current to the electrode array. The representative device further includes first and second plates 170 and 180, respectively, which overlie the outward surfaces of blocks 110 and 120, respectively. Plates 170 and 180 can reinforce the assembly. Plates 170 and 180 are preferably steel plates.

Figure 6A:
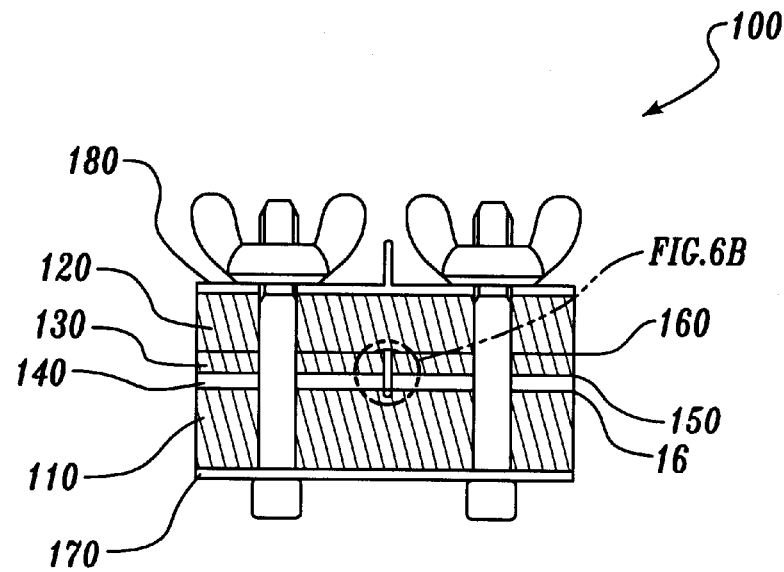
FIGS. 6A and 6B are a side plan view and a cross-sectional view of a representative device formed in accordance with the present invention.
Figure 6B:
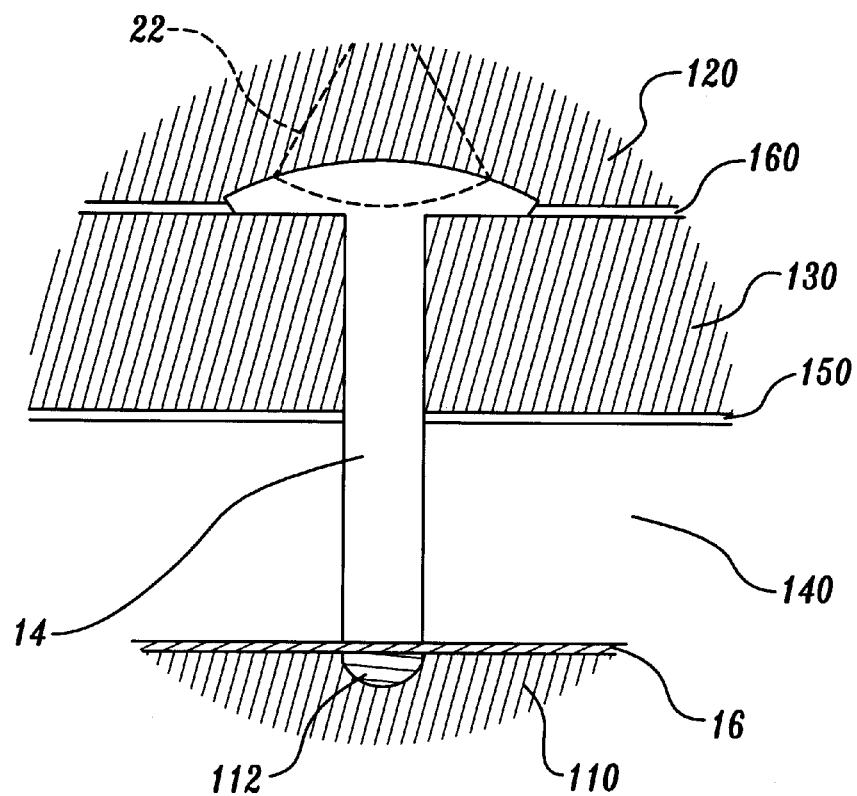

FIG. 6A and 6B are cross-sectional views of a portion of the representative device described above. Referring to FIG. 6B, device 100 includes blocks 110 and 120 and sheets 130 and 140. Intermediate block 110 and sheet 140 is porous member 16 which divides the focusing chamber into separation chamber 12 and electrode chamber 14. Sheet 140 serves as a spacer for adjusting the depth of electrode chamber 14 and, accordingly, the thickness of sheet 140 can be varied as desired. Sheet 140 is a resilient sheet and also serves to seal block 110 to the remaining components of the assembly.

Intermediate sheet 140 and sheet 130 is sealant layer 150. Sealant layer 150 includes a sealant that effectively joins sheet 140 to sheet 130 and prevents liquid from escaping the electrode chamber. Intermediate block 120 and sheet 130 is adhesive layer 160. Adhesive layer 160 includes an adhesive that effectively joins sheet 130 to block 120.

A representative device of the invention including a focusing chamber was formed from two blocks of 15×6×1.2 cm$^3$ PLEXIGLAS and a 0.3 cm thick TEFLON spacer. The front block, which houses the separation chamber (i.e., separation column or electrochromatography column), has a trough 8×0.1×0.05 cm$^3$ machined into it, the rear block, which houses 50 controllable electrodes, has a trough 6.4× 0.3×1.5 cm$^3$, and the spacer has a 6.5×0.2 cm$^2$ slot machined through it. The trough in the front block is isolated from the spacer by dialysis membrane (i.e., porous membrane) and packed with chromatography media (e.g., 4.5 $\mu$m NovaPak Diol from Waters). The rear trough and slot admit a recirculating buffer that can have the same composition as the running (i.e., elution) buffer, acts both as coolant, anolyte, or catholyte, and removes electrolysis products from electrode array. Because the coolant is in contact with the separation column via a dialysis membrane, the coolant can also be used to dialyze the running buffer to exchange salts or other low molecular weight solutes. The coolant inlet and outlet are shown in FIGS. 4 and 5.

Outside of the focusing chamber, the coolant buffer is circulated through a glass heat-exchange reservoir submerged in an ice bath. From here the coolant is introduced into the bottom of the focusing chamber and is passed over the electrodes at ~15 mL/s using a centrifugal pump (Cole-Parmer). A syringe pump controls the flow of the running buffer through the packed bed at 15–150 $\mu$L/h. The running buffer enters the column in the upper flow inlet on the front face and exits from the lower flow outlet on the front face. All lines are PEEK with flangeless fittings; sample is loaded through a 10-$\mu$L loop on a six-port injection valve (Upchurch).

The 50 chamber electrodes are made from 0.25-mm-o.d. platinum wire (Aldrich Chemical), mounted in the rear PLEXIGLAS block with a 0.05-in. pitch, and are connected to a SCSI ribbon cable using SMS-series microstrips (Samtec). Each of the SCSI leads is connected to its own printed-circuit (PC) monitor/controller board mounted on the wire wrap motherboard. Each monitor/controller board is segregated into three areas: high voltage, monitoring, and control. The high-voltage area isolates the chamber electrode voltages, which can be as high as 600 V, from the relatively sensitive electronics used to measure and adjust the electrode voltages. The monitor area of each PC board scales down the electrode voltage by ~100 x and sends this signal to a commercial thermocouple board which digitizes the signal before sending it to the computer. The computer scans all 50 electrodes, compares these readings with the programmed profile, and sends a digital signal to a set of 50 DACs which tell the optical isolators to adjust the effective resistance of high-voltage line to reduce the departure of the measured electrode voltages from the programmed voltage profile. A complete scan/control cycle of the 50 controllers is taken every second. Each of the 50 controllers is mounted vertically on a wire-wrapped motherboard; power to the controllers motherboard is drawn from the computer. A 600-V power supply (Xantrex) provides current to the column's 50 high-voltage electrodes via the 50 voltage controllers.

The device is operated as follows. After the recirculating coolant has reached operating temperature and the packed column has been cleaned, e.g., with 7 M urea, and equilibrated with running buffer, 10 $\mu$L of protein solution is injected into the column, which has a packed volume of 28 $\mu$L exposed to the 50 controlled electrodes, using a standard sample loop. Before protein reaches the outlet, the controller is booted using a default voltage pattern and the power supply is brought up to a voltage in the range 200–600 V. The operator then selects the initial electric field gradient, and the computer program adjusts the electrode voltages until this gradient is attained, typically less than 5 min. from a "cold" start.

The following materials were used in demonstrating the device and method of the invention. Chemicals and biochemicals were purchased from Sigma. Bare silica HPLC sorbents were purchased from Sigma and Methacrylate SEC packings from Tosohaus. Various sizes of Symmetry packings (3.5–12 $\mu$m) were donated from Waters Corporation. Fluorescent tags were purchased from Molecular Probes (Eugene, Oreg.). Sheets of 6k MWCO dialysis membranes were purchased from Cole-Parmer.

Figure 7:
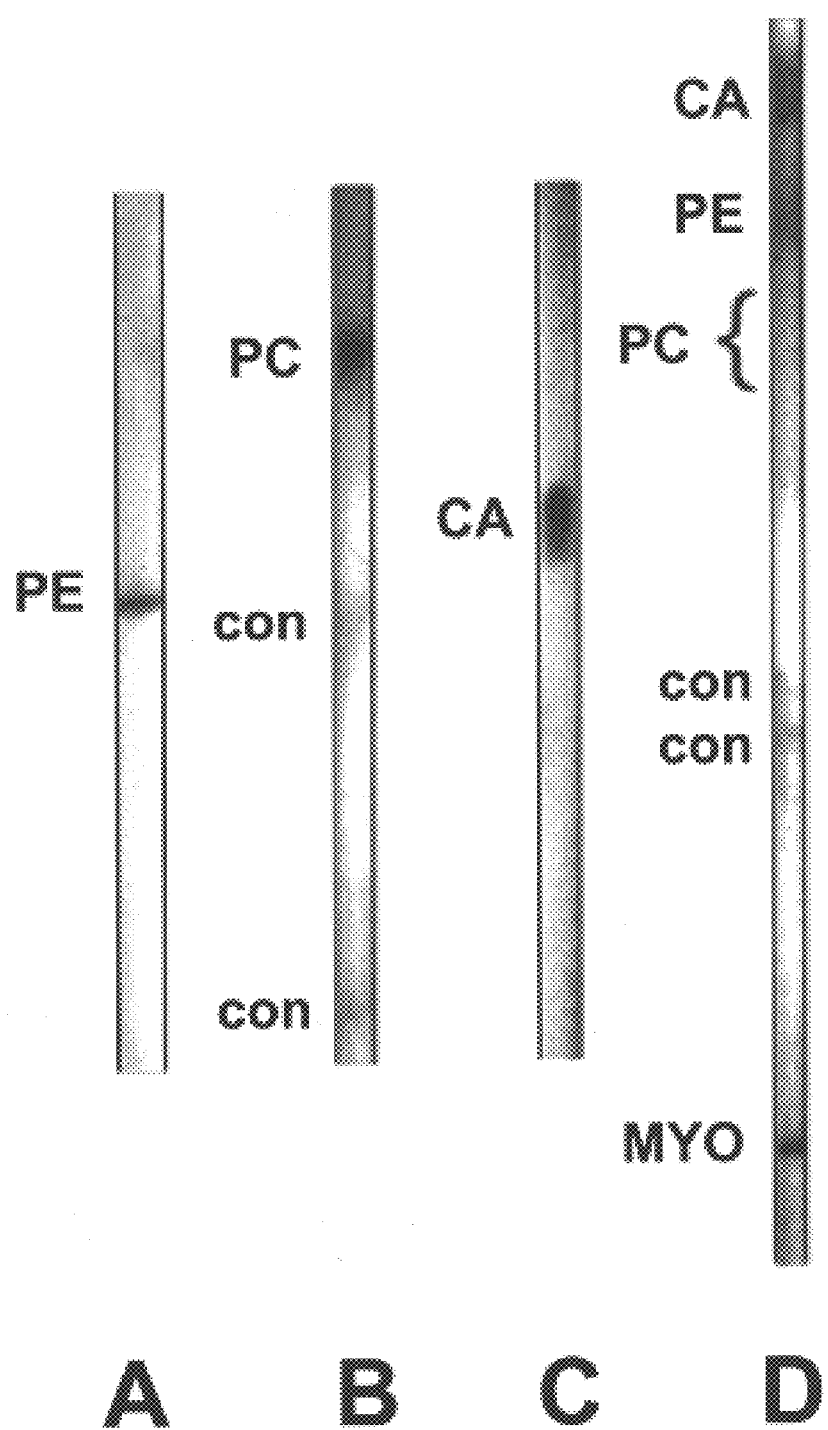
FIGS. 7A–D are digitized images of Phycoerythrin (PE); Phycocyanine (PC) showing two contaminants (con); carbonic anhydrase labeled with Texas Red (CA); and a cocktail of PE, PC, CA, and myoglobin (MYO), respectively, focused in accordance with present invention.
Figure 8:
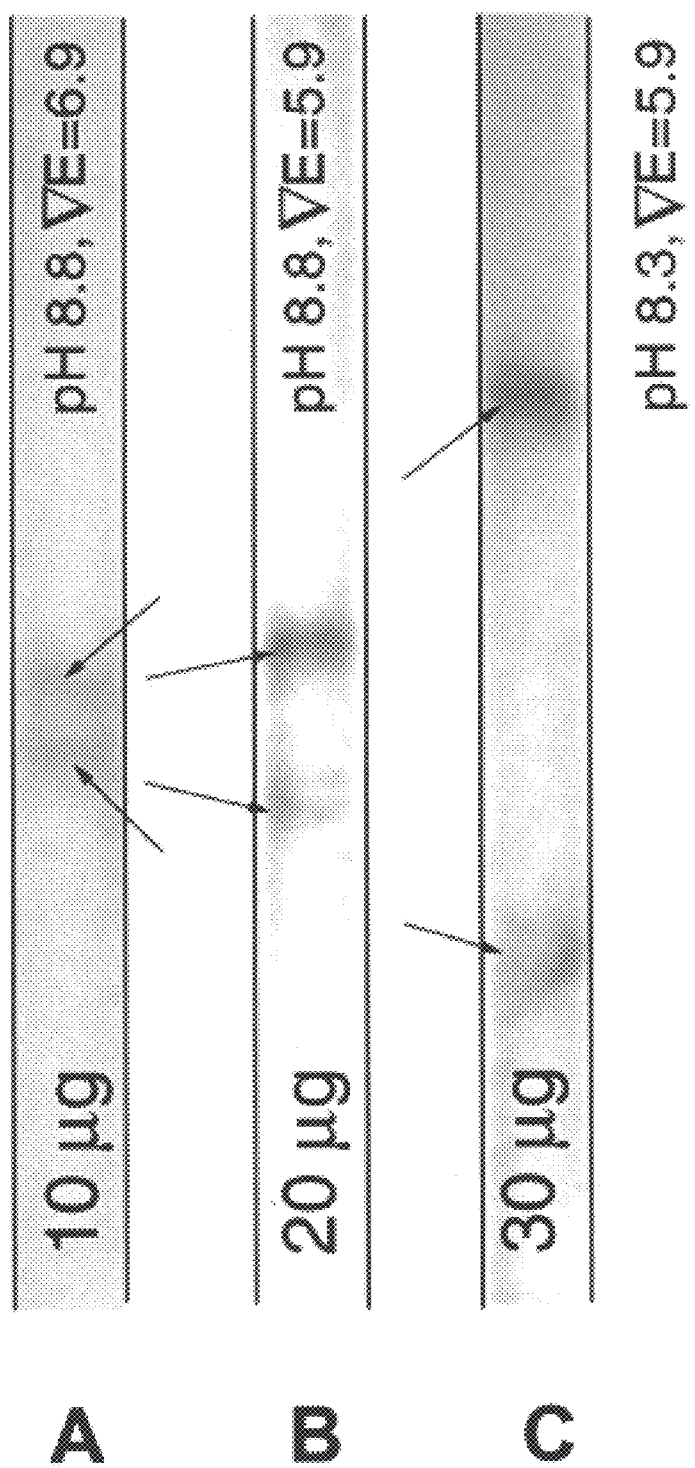
FIGS. 8A–C are digitized images of myoglobin (Sigma IEF-grade) in 10 mM tris-phosphate buffer focused in accordance with the present invention at pH 8.8, 400V, and $\nabla E=6.9$, two bands about 0.5 mm thick are separated by about 0.5 mm (A); reducing the electric field gradient to $\nabla E=5.9$ increases resolution (B); and reducing the pH in the coolant circuit to 8.3 further improves band resolution (C)
Figure 9:
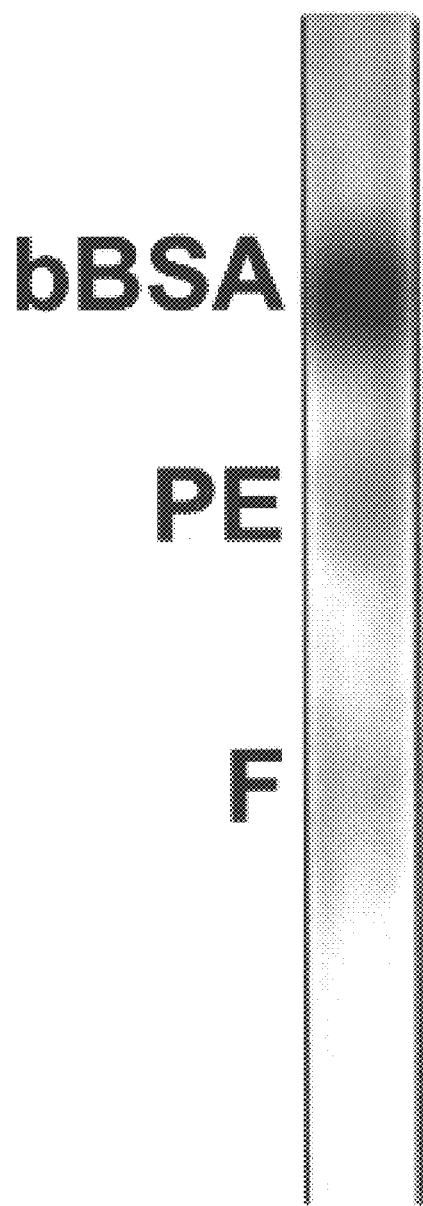
FIG. 9 is a digitalized image of a cocktail of bovine serum albumin labeled with bromophenol blue (bBSA), PE, and ferritin (F) focused at pH 8.7 and $\nabla E=3.7$ in accordance with the present invention.

Typical focusing results achieved with the device of the invention are presented in FIGS. 7–9, which are digitized images of naturally colored or artificially labeled proteins dynamically focused in an electric field gradient. In each of these figures, the flow in the packed section of the column is from top to bottom and the voltage gradient is greatest near the outlet, vanishes at the inlet, and is linear over the 2.5-in. length of the electrode section. In all of these experiments, the first 49 array electrodes are anodes while the last electrode is a cathode set to ground and the electric field strength is linear.

The proteins and run conditions used in these experiments are listed in Table 1. Individual protein bands (FIGS. 7A–C) take 10 to 30 min. to focus depending on the flow rate of the running buffer. The bands formed have roughly the baseline width predicted by the linear theory discussed below and reach concentrations in the range of 5–50 mg/mL even without subtracting the nonaccessible volume of the packing. For example, in FIG. 7A, the phycoerythrin band is less than 0.2 mm thick, 1.0 mm wide, and 0.5 mm deep and contains 2.5 $\mu$g of protein which translates to an apparent focused concentration of roughly 25 mg/mL.

TABLE 1

Run Conditions for Proteins in FIGS. 7–9[a]

| FIG. | Protein (Sigma) | Catalog No. | pH | $\nabla E$ (V/cm$^2$) | Flow ($\mu$L/h) | Applied Voltage (V) | Protein Mass Loaded ($\mu$g) | Load Protein Conc (mg/mL) |
|---|---|---|---|---|---|---|---|---|
| 7a | (R)-phycoerythrin (PE) | P 0159 | 7.0 | 13.0 | 44 | 300 | 2.5 | 0.25 |
| 7b | (R)-phycocyanin (PC) | P 1536 | 7.0 | 13.0 | 42 | 300 | 5.0 | 0.50 |

TABLE 1-continued

Run Conditions for Proteins in FIGS. 7–9[a]

| FIG. | Protein (Sigma) | Catalog No. | pH | $\nabla E$ (V/cm$^2$) | Flow ($\mu$L/h) | Applied Voltage (V) | Protein Mass Loaded ($\mu$g) | Load Protein Conc (mg/mL) |
|---|---|---|---|---|---|---|---|---|
| 7c | carbonic anhydrase (CA) | C 6653 | 7.0 | 9.3 | 40 | 300 | 5.0 | 0.50 |
| 7d | carbonic anhydrase | C 6653 | 8.0 | 13.0 | 39 | 300 | 4.4 | 0.44 |
|  | (R)-phycoerythrin | P 0159 |  |  |  |  | 2.8 | 0.28 |
|  | (R)-phycocyanin | P 1536 |  |  |  |  | 2.5 | 0.25 |
|  | myoglobin (MYO) | M 9267 |  |  |  |  | 5.0 | 0.50 |
| 8a | myoglobin | M 9267 | 8.8 | 6.9 | 100 | 400 | 10.0 | 1.0 |
| 8b |  |  | 8.8 | 5.9 |  |  |  | 2.0 |
| 8c |  |  | 8.4 | 5.9 |  |  |  | 3.0 |
|  | bovine serum albumin (bBSA) |  | 8.7 | 3.7 | 138 | 300 | 2.0 | 0.20 |
|  | (R)-phycoerythrin | P 0159 |  |  |  |  | 2.0 | 0.20 |
|  | ferritin (F) | F 4503 |  |  |  |  | 3.0 | 0.30 |

[a]Conditions: 10 mM tris-phosphate buffer on 4.5 $\mu$m NovaPak-Diol packing.

When multiple proteins are run, as is the case in FIG. 7D, it is sometimes difficult to set a linear field gradient where all of the proteins can be retained in the column and baseline separated at the same time. This is due in part to the wide variation in mobilities in this particular group of proteins and, to a greater extent, to the tendency of the concentrated protein bands to merge into isotachophoretic bands if they come too close to one another.

FIG. 8 shows how separation conditions can be modified by the operator during a run to improve resolution. In FIG. 8A, IEF-grade marker myoglobin is separated into two bands. In FIG. 8B, the electric field gradient has been reduced, and a few minutes later, the bands have moved further apart. In FIG. 8C, the pH of the recirculating buffer/coolant has been lowered from 8.8 to 8.4 over a period of 30 min. and the distance between the bands has increased further.

FIG. 9 is a protein cocktail containing bovine serum albumin labeled with bromophenol blue (bBSA), PE, and ferritin and illustrates that other groups of proteins whose mobilities are similar can be baseline-separated with relative ease.

The results demonstrate that, in accordance with the present invention, it is possible to establish and manipulate an electric field gradient by using a computer-controlled array of electrodes. In combination with a continuous counterflow of buffer, this gradient can be used to simultaneously separate proteins whose apparent mobilities differ by less than 10% and to focus them to concentrations in excess of 50 mg/ml in an electrochromatography format.

Most, if not all, members of the family of electrophoretic focusing techniques can be described by the simple flux equation, $$N_{p,x} = -D_p \frac{dc_p}{dx} + \left( \langle u_{p,x} \rangle + z_p \omega_p \frac{I_x}{\sigma} \right) c_p = 0 \qquad (1)$$

where $N_{p,x}$ is the molar flux of protein along the x-axis of the electric field. For focused protein bands, the flux is set equal to zero to indicate that the bands are stationary. Equation 1 is composed of a dispersive term, a convective term, and an electrophoretic term where $c_p$ is the protein concentration, $D_p$ is a diffusion or dispersion coefficient, $u_{p,x}$ is the apparent hydrodynamic velocity along the x-axis, $z_p$ is the protein charge, $\omega_p$ is the protein mobility, $I_x$ is the current density, and $\sigma$ is the electrical conductivity. For proteins to focus, it is necessary that at least one of the terms in parentheses varies so that their sum forms a gradient which vanishes at a discrete point in the chamber and which pushes the protein toward that point regardless of its initial location. Focusing occurs at the point in the chamber where the sum of the terms in parentheses vanishes.

Setting the sum of the terms in parentheses in Equation 1 equal to zero, it is seen that focusing may be accomplished in at least five different ways: (a) in a pH gradient with $u_p=0$, proteins focus at the point where the net charge on the protein vanishes, i.e., $z_p=0$, as is the case with isoelectric focusing (IEF); (b) in a gradient in $u_{p,x}$ with $z_p$, I, and $\sigma$ held constant, which corresponds to O'Farrell's counteracting chromatographic electrophoresis; (c) in a gradient in $\omega_p$ with $u_{p,x}$, $z_p$, I, and $\sigma$ constant, e.g., focusing a protein in a urea gradient. With $u_p$ held constant, proteins can be focused by (d) forming gradients in I, as was done by Koegler and Ivory, *J. Chromatogr.*, A 1996, 229, 229–236, or (e) forming gradients in a, as was done by Greenlee and Ivory, *Biotechnol. Prog.* 1998, 14, 300–309. Both of these approaches generate gradients in the electric field similar in many respects to the gradients generated by the instrument described above.

Setting $I_x = I_{0,x} + xI_{1,x}$ to form a linear gradient in the current, the focal point is found at $$x_f = -\left( \frac{\langle u_{p,x} \rangle}{z_p \omega_p I_{1,x}} + \frac{I_{0,x}}{I_{1,x}} \right) \qquad (2)$$

and, integrating Equation 1, the concentration is given by $$c_p = \frac{M_T}{W} \sqrt{\frac{Z_p \omega_p I_{1,x}}{2 \pi \sigma D_p}} \exp\left[ -\frac{Z_p \omega_p I_{1,x}}{2 \sigma D_p} (x - x_f)^2 \right] \qquad (3)$$

which yields a Gaussian distribution in the focused band. The standard deviation, X, of the peak around the focal point is then $$x = \sqrt{\sigma D_p / z_p \omega_p I_{1,x}} \qquad (4)$$

where $M_T$ is the total mass in the focusing chamber and W is the perimeter of the chamber. Note that focused bands are made thinner by low conductivities and steep current gradients. Conversely, resolution, R $$R = \frac{1}{2}\sqrt{\frac{\langle u_{p,x}\rangle^2 \sigma}{D_p l_{1,x}}} \left| \frac{1}{\sqrt{z_{p,1}\omega_{p,1}}} - \frac{1}{\sqrt{z_{p,2}\omega_{p,2}}} \right| \quad (5)$$

is improved by reducing the gradient, raising the conductivity, and increasing the velocity of the running buffer. The simple linear model presented above does a good job of predicting protein location and baseline width when bands are completely resolved. However, because the model ignores nonlinear coupling between the electric field and the ions in solution, it cannot accurately describe overlapping or contiguous bands. A more detailed version of this model that can handle these situations is given by Koegler and Ivory. *Biotechnol. Prog.* 1996, 12, 822–836.

Figure 10:
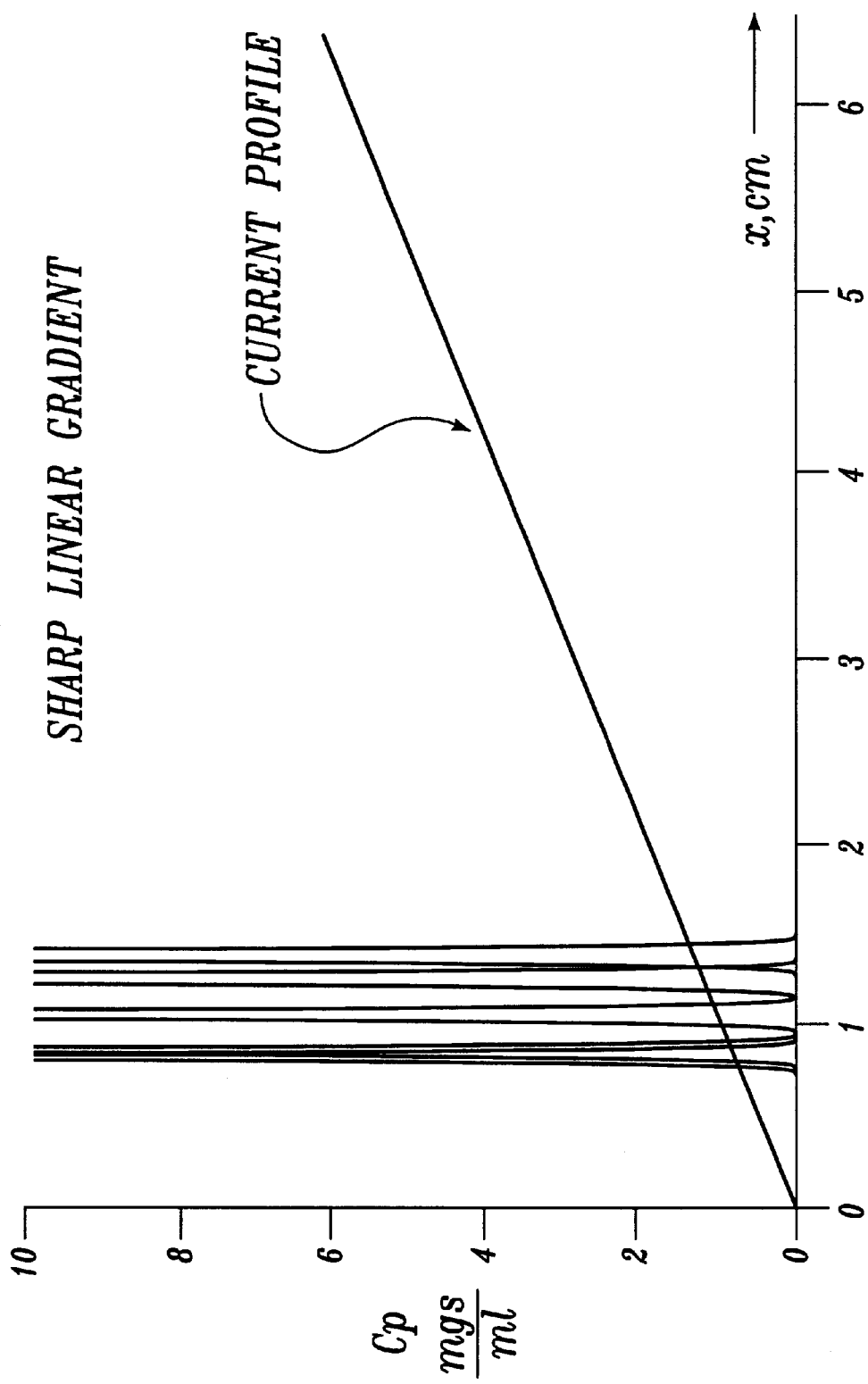
FIG. 10 is a graph of five simulated proteins focused in a sharp linear current gradient which goes from zero current at the inlet, x=0, to about 6.5 mA at the column outlet, x=6.35 cm with the two fastest peaks overlapping near x=0.8 cm.
Figure 11:
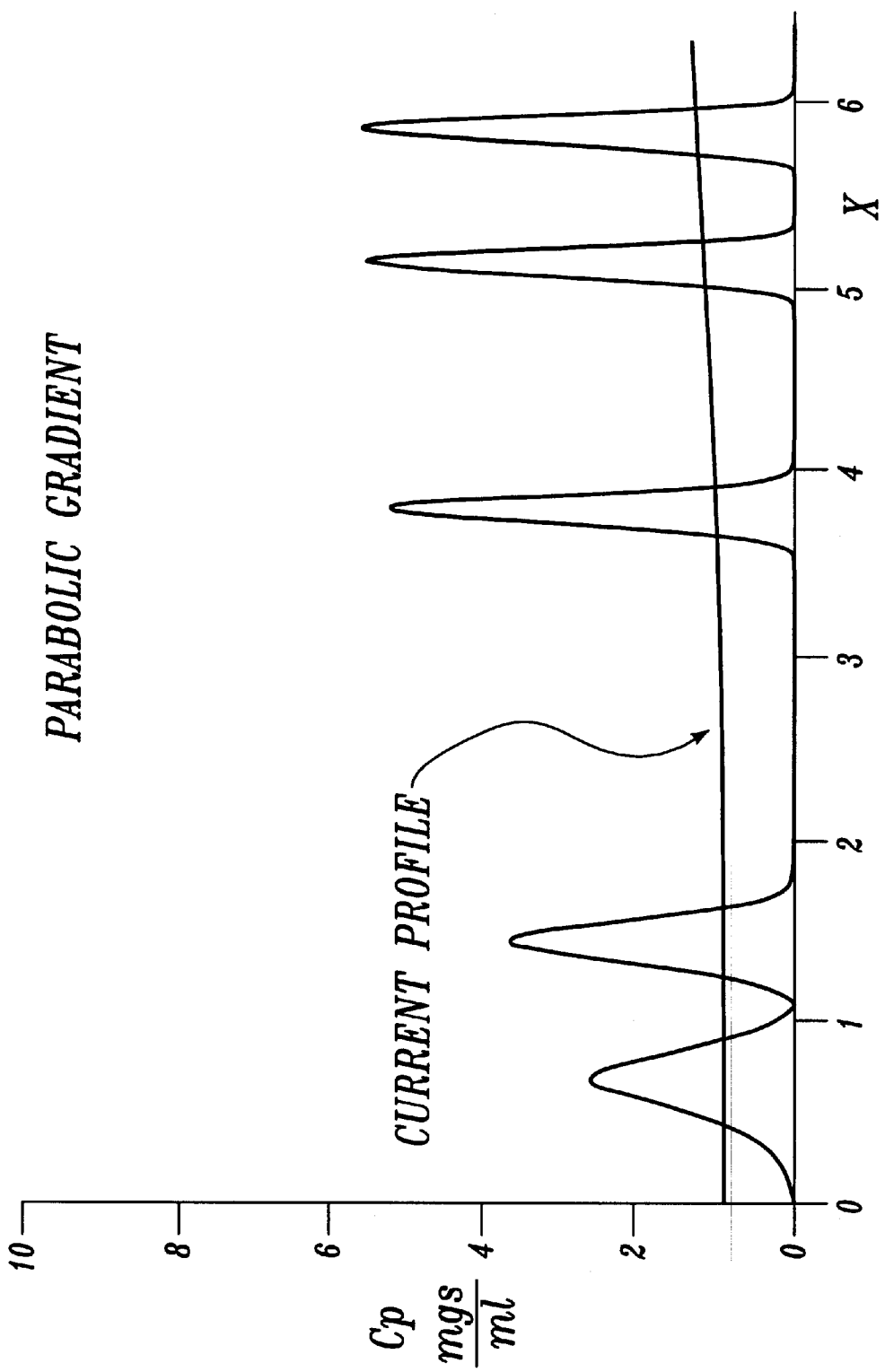
FIG. 11 is a graph of a parabolic gradient illustrating complete separation of the fast protein while keeping the slower peaks apart by flattening the front of the gradient and steepening the rear of the gradient.
Figure 12:
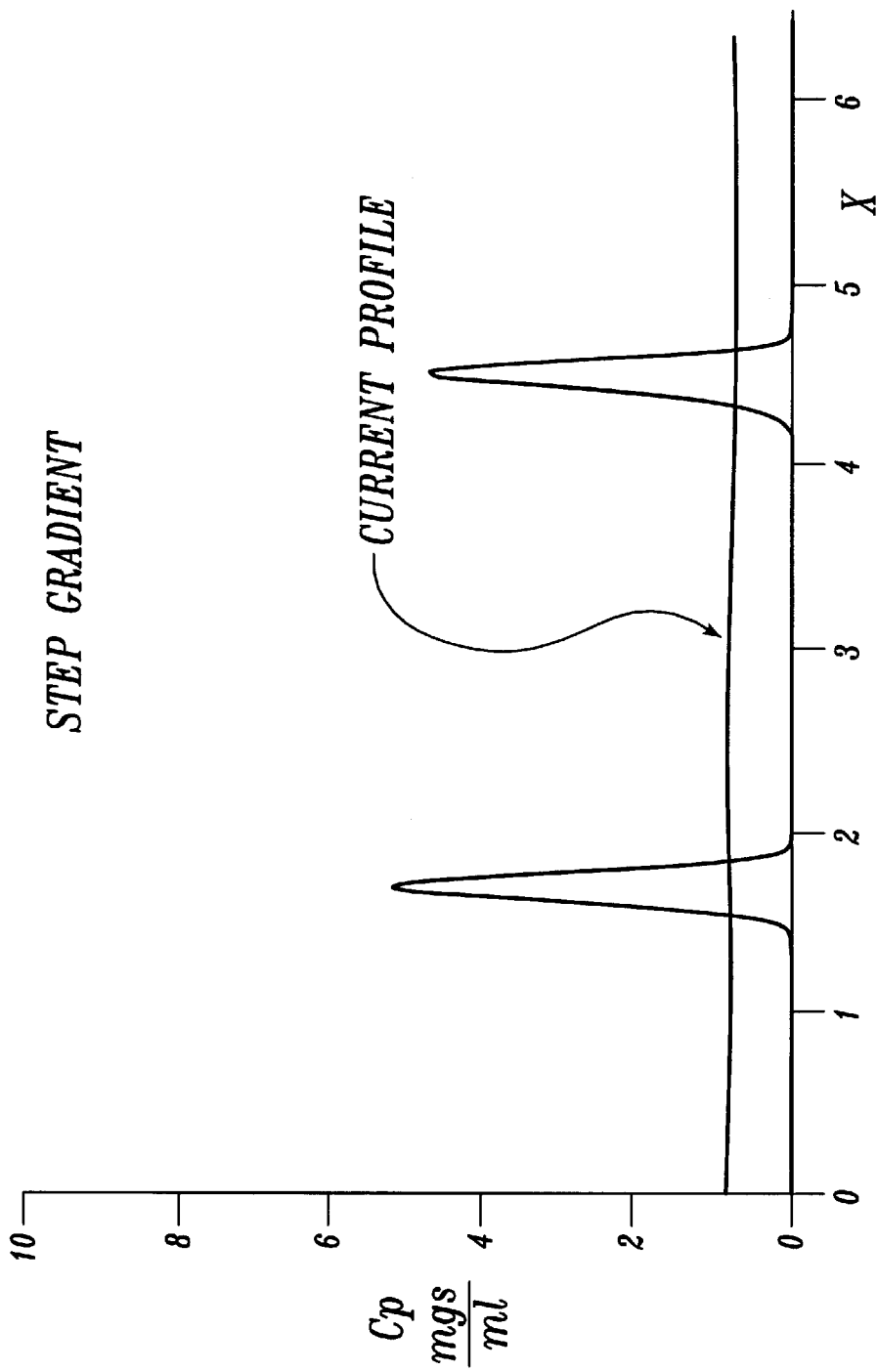
FIG. 12 is a graph of a step gradient to sharpen peaks and set their positions precisely, the two small step changes in the electric field located at x=1.5 and 4.5 cm allow the fast proteins to remain separated and tightly focused.
Figure 13A:
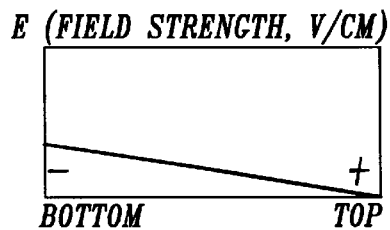
FIG. 13 is a schematic representation of two approaches for conducting electric field gradient focusing in accordance with the present invention.
Figure 13B:
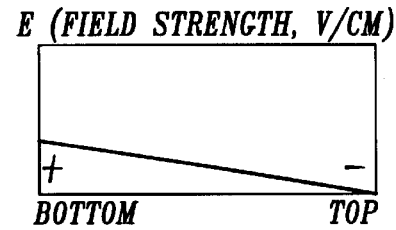
Figure 13C:
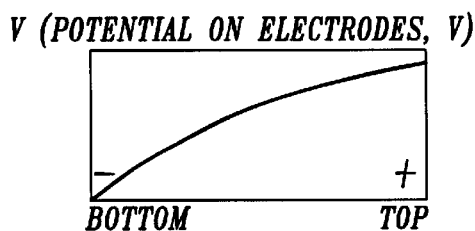
Figure 13D:
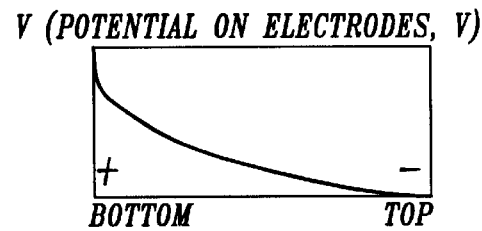
Figure 13E:
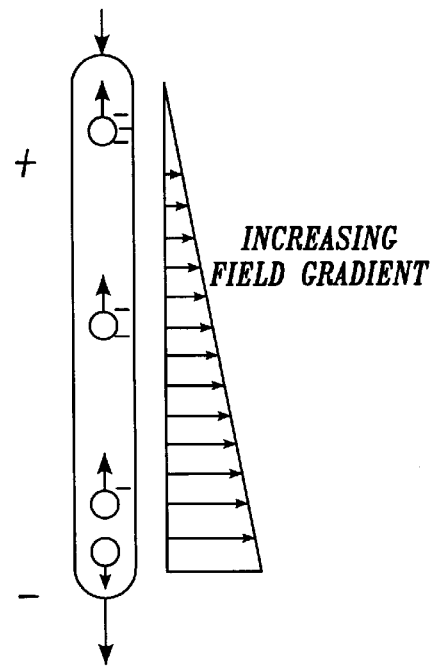
Figure 13F:
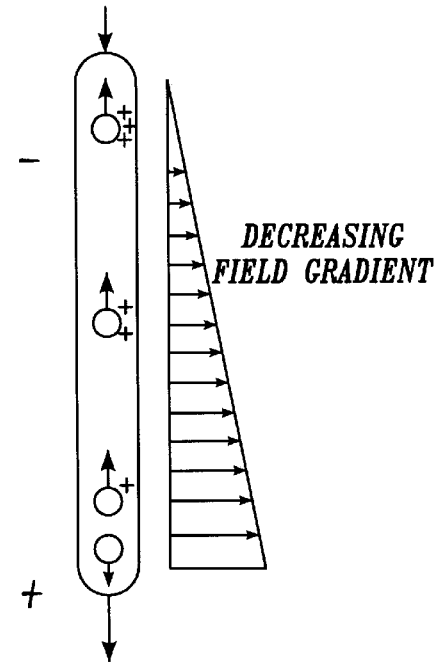

The performance of the device and method of the invention under various conditions can be simulated. The linear model can be used to explore the advantages of electronically controlled focusing, specifically, by adjusting the field parameters to enhance resolution during a run. For example, a sharp linear gradient is shown in FIG. 10 for five recombinant protein isoforms with the electrophoretic mobilities given in Table 2 focused near the top of the DFGF chamber. As shown in FIG. 11, these proteins might first be moved as a unit to the center of the chamber, e.g., by increasing the flow rate, and then spread over the entire length of the column by expanding the electric field so that the fastest peak is near the chamber inlet and the slowest peak is near the outlet. By flattening and reducing the electric field gradient, the three low-mobility peaks could be eluted from the chamber while the two fastest peaks are retained. After switching to step changes in the electric field the remaining two peaks, whose mobilities differ by ~3%, can be completely separated and individually eluted from the chamber as shown in FIG. 12.

TABLE 2

| Simulation Electrophoretic Mobilities | |
| --- | --- |
| fast peak | $-1.65 \times 10^{-5}$ cm$^2$/V-s |
| | $-1.60 \times 10^{-5}$ cm$^2$/V-s |
| | $-1.30 \times 10^{-5}$ cm$^2$/V-s |
| | $-1.10 \times 10^{-5}$ cm$^2$/V-s |
| slow peak | $-1.00 \times 10^{-5}$ cm$^2$/V-s |

This simulation demonstrates that it is possible to establish and manipulate an electric field gradient by using a computer-controlled electrode array. In combination with a continuous flow of buffer, this gradient can be used to simultaneously separate and focus proteins as well as other charged molecules at concentrations in excess of 50 mg/mL in a packed-column format.

DFGF cannot replace IEF as an analytical technique. DFGF cannot work at the isoelectric point (pI) because the proteins mobilities vanish at that point. However, DFGF does effectively extend the pH range over which focusing can take place to include native buffers as well as non-native, denaturing, and reducing conditions. A resultant advantage is that focusing can be accomplished away from a protein's pI, thus avoiding the precipitates that often form near the isoelectric point and making it preferable to IEF as a preparative technique.

Although the above examples illustrate the use of linear electric field gradients, the software can be modified to allow point-by-point adjustment of the field including reversing the field to aid in elution of fractionated bands, isolating and mobilizing a single protein band, or stepping the gradient to improve processing capacity. In addition, because the electronic controller and the DFGF technique are largely independent of chamber capacity, there is no reason DFGF cannot be applied to other types of electrophoresis equipment operating at larger or smaller scales.

The above examples included colored and labeled proteins. In another embodiment, optical or other detectors can be mounted on the chamber to provide real-time monitoring of the separation. Such monitoring allows for computer detection of various peaks, optimization of the separation by locally adjusting the field gradient to tease refractory proteins apart, and then pull off those peaks that were selected by the operator either before or during a separation.

The principles of the method and device of the invention will be better understood by reference to the following discussion.

In zone electrophoresis, an electric field causes the differential transport of charged species. Voltage is applied across the separation path, leading to the migration of charged species away from the starting band and along the path. Separation develops because of differences in migration velocities, which are proportional to the electric field, E. A simple equation is given by $$U_i = \mu_i E \quad (6)$$

where $\mu$ is the electrophoretic mobility of the species which depends on the electrical charge, which determines how vigorously they are driven by the applied voltage, and the degree of frictional drag, which differentially oppose their electrophoretic motion (Mosher, R. A., Saville, D. A., and Thormann, W., THE DYNAMICS OF ELECTROPHORESIS, VCH Publishers, Inc., New York (1991)).

Because the charge of the species can be positive or negative, the electrophoretic mobility has direction with respect to the direction of the potential gradient, as does the migration velocity, U. The surface is strongly dependent on the ionic strength and this affects the particle mobility.

At conditions approaching infinite dilution, the one-dimensional motion of a charged species can be described by the flux equation.

$$N_i(x) = D_i \frac{dc_i}{dx} + (u_i + \mu_i E) c_i \quad (7)$$

where $u_i$ is the chromatographic velocity (or convective velocity), $c_i$ is the concentration of the ion, and $D_i$ is the diffusion coefficient of specie i. In order for species i to focus it is necessary that at least one of the terms in parentheses vary with respect to x so that their sum forms a gradient which vanishes at a point in the chamber. Focusing then occurs at the point in the chamber where these terms vanish.

In accord with this condition, there exist many ways to accomplish focusing. First, by forming a gradient in chromatographic velocity $u_i$, with $\mu_i$ and E held constant and counter-balanced with $u_i$, which corresponds to CACE; second, by forming a gradient in $\mu_i$, which can be accomplished in a pH gradient, with $u_i=0$ and held E constant, as in the case in IEF; third, by creating a gradient in E, with $u_i$ and $\mu_i$ held constant, that is the case in FGF.

In all the above cases, the efficacy of separation depends on the concentration profile of solute in the steady-state zones and layers. It is worth reflecting on the physical origin of steady-state conditions in separative transport. Any narrow pulse of solute will tend to diff-use outward, and its profile can be maintained in a steady-state condition only if some transport process exactly balances diffusion. Such transport may be induced by flow or external fields. The transport tends to focus solute toward a given point, and keeps the solute compressed as a narrow zone around that point.

For FGF, the concentration profile of solute on the simplest field gradient can be obtained analytically. A linear electric field gradient can be described as $$E(x) = E_1 x + E_o \quad (8)$$

where $E_o$ is the average field strength applied on the chamber and $E_1$ is the increase in field strength per unit length. If A is the cross section area of the chamber, and $M_i$ is the total moles of the i specie. Solving Equation (6), we obtain the concentration profile for species i $$C_1(x) = \frac{1}{\sqrt{2\pi}} \frac{M_i}{\sigma_i A} \exp\left[-\frac{(x - \chi_i)^2}{2\sigma_i^2}\right] \quad (9)$$

which is a Gaussian distribution with focal point X and variance $\sigma^2$ given by $$\chi_i = -\frac{u_i + \mu_i E_o}{\mu_i E_1} \quad (10)$$

$$\sigma_i^2 = -\frac{D_i}{\mu_i E_1} \quad (11)$$

The solution to this simple model indicates that, in order to focus a protein in an electric field gradient, $u_i$ and $\mu_i E_1$ must have opposite sign. There are two cases that fit this condition, which are shown in FIG. 13. First, the negatively charged proteins focus in an increasing field gradient with the electric field in the same direction as the convective flow of buffer (A). Second, positively charged proteins focus in a decreasing field gradient with the electric field in opposite direction as the convective flow (B). The amount of charge carried on protein molecules are closely related to the pH of the buffer and are different from species to species. The migration rate is directly proportional to the amount of charge carried which is different from specie to specie. Therefore, distinct stationary accumulation zones for differently charged species are generated along the column. In order to focus the target protein in the chamber, the direction of electric field, the slope of field gradient and the pH of the elution buffer must be matched. Otherwise, the target protein will be flushed out or concentrated at the very top of the column, allowing no separation at all.

The variance $\sigma_i^2$, which is a measure of the width of the focused protein peak, suggests that the focused band will be tighter and more concentrated if the diffusion coefficient is decreased or if the slope of the field gradient is increased. However, increasing the slope of the gradient will move the focused bands closer together, so that resolution will decrease. There is a trade-off between the resolution and the shape of the peak. Equation 9 indicates that electrophoretic mobility, the convective velocity and the field gradient determine the position of the focused band in the column.

Figure 14:
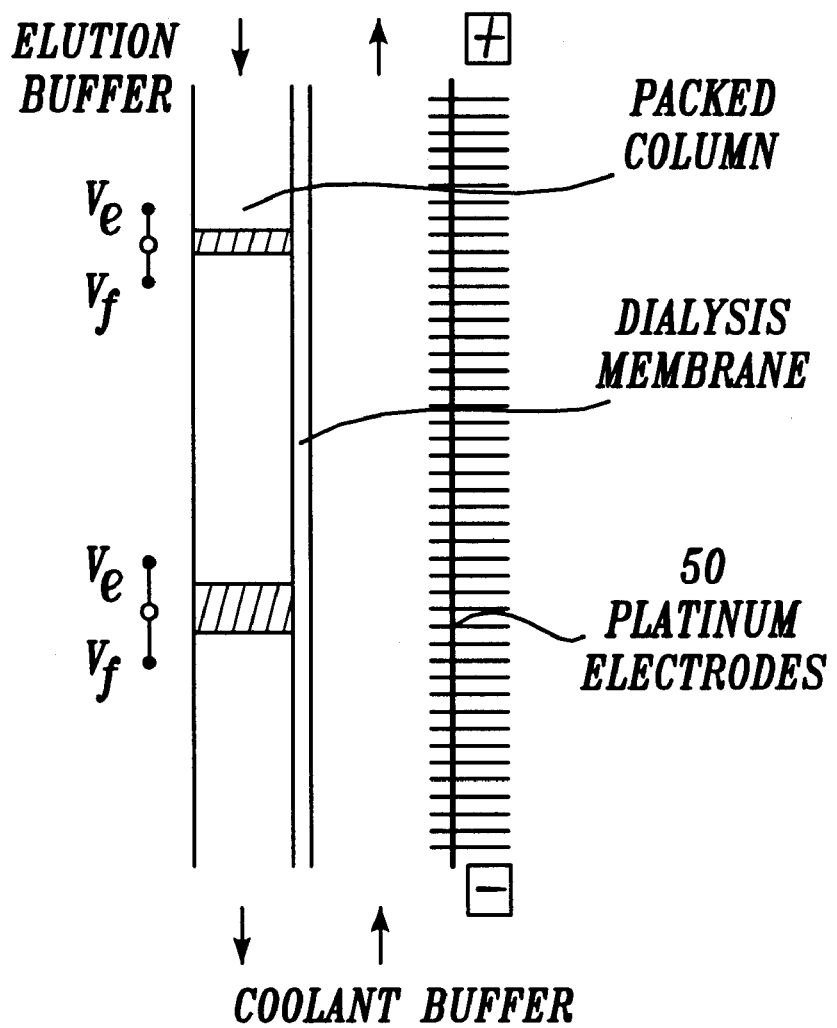
FIG. 14 is a schematic drawing of a representative device formed in accordance with the present invention.
Figure 15A:
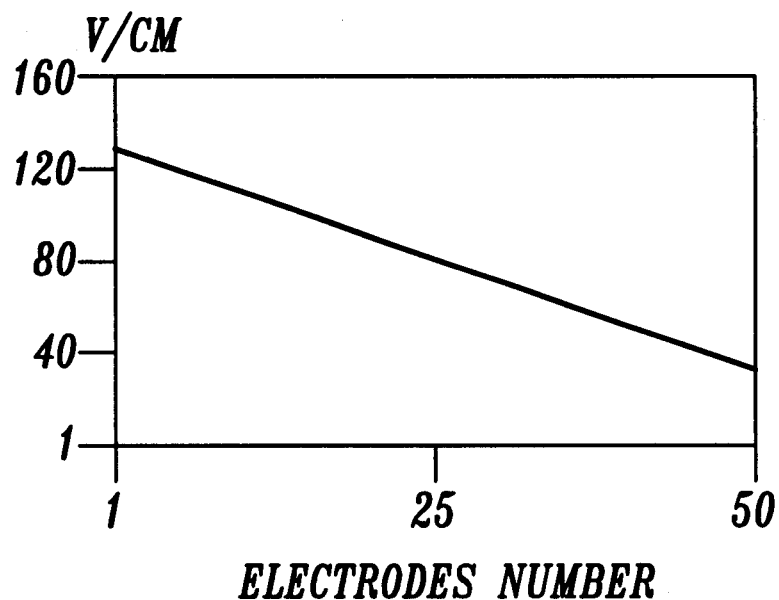
FIGS. 15A and 15B are schematic diagrams of the field strength profile (A) and potential profile (B) of a linear field gradient (15.5 v/cm$^2$) formed in accordance with the present invention.
Figure 15B:
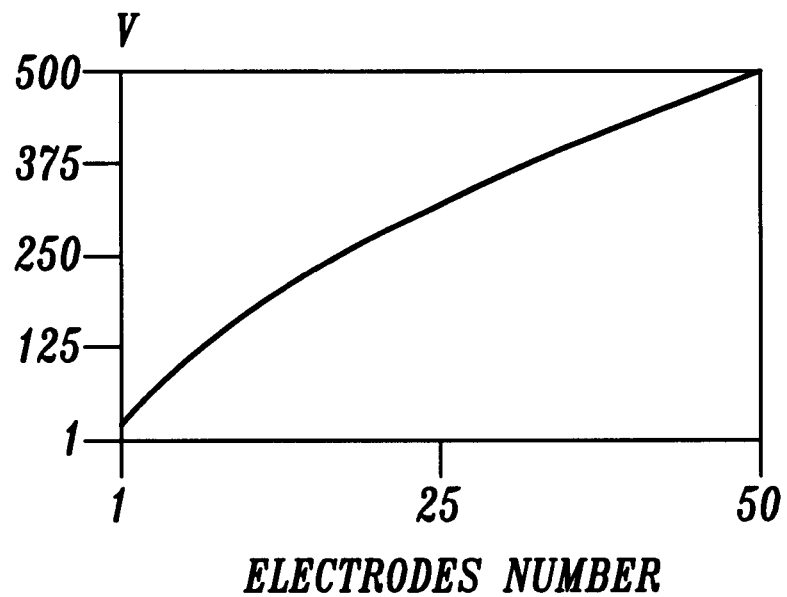

The present invention relates to dynamic field gradient focusing (DFGF). Unlike the fixed field gradient design in the prototype apparatus in Koegler's previous work, in the present invention (see FIG. 14), dynamic electric field gradients are created by a computer-controlled external circuit, which manipulates the field strength between each pair of adjacent electrodes. With the circuits and the controlling software we developed, varying field strength along the separation chamber is achieved. A linear electric field gradient created by the circuits is shown in FIG. 15.

In a typical DFGF operation, the electrophoretic force on charged species and the driving force by which the samples move through the column are all directly opposed to each other in direction. The driving force can be a summary of the influences of the convective flow of the elution buffer, the chromatographic flow and the electroosmotic flow (if the packing material surface is charged). The combined influence on a particular specie can be precisely canceled out to achieve a steady-state at a unique point in the column.

The porous membrane is conductive to heat and buffer ions but not to bulk fluid flow. With this design, the electrodes are isolated from the packed column (i.e., separation chamber) to avoid disruption of the laminar flow by gas generation or denaturation of protein by contact with the electrodes. The same buffer is used for the packed column and the electrode chamber to ensure the ion balance between the two sides. The recycle buffer goes upward in the electrode chamber, effectively removing the tiny gas bubbles generated at the electrodes and acts as coolant to remove the Joule heat generated. Another important role of the recycle buffer is to conduct the electric field gradient through the dialysis membrane to the packed column. In the packed column, the elution buffer is injected from top to bottom to prevent the beads from fluidizing.

For practical DFGF operation, Equation 8 is too simple to predict the behavior of protein bands in the column. The chromatographic retarding force affects the migration of the protein sample, however, it does not affect the position of the focused band in the packed column. Instead, it shows its effect by reducing dispersion. In general, chromatography with a packed column, three main independent processes contribute to band broadening of solute zones when the migrate through the column, namely, the unevenness of flow through the packing (eddy diffusion), axial molecular diffusion and solute resistance to mass transfer between phases. In DFGF, the electrophoretic behavior of the protein molecules and buffer ions also play important roles.

First, natural convection produced by Joule heating disturbs the flow profile in the packed column. A temperature gradient in the axial direction causes an uneven distribution in the viscosity, density, and pH of the buffer, and contributes to zone broadening in the packed bed. One might argue that this problem can be overcome by reducing the conductivity of the carrier buffer, but this can only go so far before the protein concentration surpasses its solubility limit or the device develops a conductive dielectric instability Hunter, J.B., PROGRESS IN MATHEMATICAL MODELING OF CACE, IN MARCEL DEKKER, INC., C.F. Ivory, Editor, 1988, Marcel Dekker, Inc., New York. p. 875. The recycling of the coolant buffer in the DFGF apparatus greatly improves heat dissipation. For the thin column, we used (1 mm diameter), the resolution loss due to Joule heating will not likely be the major problem. However, for large scale apparatus, this should not be neglected.

The ionic strength of the buffer affects the DFGF on several aspects: the ion concentration affects the protein interaction with the packing materials, relatively high concentration buffer stabilizes the protein sample and therefore avoids precipitation and unfavorable adsorption on the surface of the packing. However, in general, high ionic strength means high conductivity of the buffer, which increases the heat generation and power consumption and, for DFGF, sets a limit for the highest applicable field strength. For charged column packing, electroosmotic flow (EOF) is generated under the action of the electric field, and is closely related to the ionic strength of the buffer used. In general, the lower the ion concentration, the higher the EOF rate.

An asymmetry in band shape is frequently seen in zone electrophoresis as well as in DFGF, which is always present when the mobilities of sample and buffer ions are unequal. DFGF is mainly used for the separation of high molecular weight components, such as proteins, peptides and probably nucleic acids. In general, the sample has smaller diffusion coefficients and electrophoretic mobilities than the buffer ions, and, as a result, the sample zone will often have a sharp frontal boundary. The migrational dispersion due to the electric field is usually much larger than diffusional dispersion. The same phenomena have been observed in DFGF.

At high sample concentrations, the shape of the focused band is not expected to follow the Gaussian distribution predicted by the model. The field gradient itself will distort at the point where proteins focus Koegler, W. S. and Ivory, C. F., "Focusing Proteins in an Electric Field Gradient," *J Chromatography*, 1996. 229:p. 229–236, the concentration profile will deviate from the symmetrical Gaussian distribution and the bands of components with similar mobilities will overlap.

The field gradient affects resolution and capacity. With a shallow field gradient, more protein can be accommodated on the column before the bands overlap, therefore, the capacity can be increased by using a shallow gradient. The disadvantage is that proteins with large differences in their mobilities cannot focus simultaneously on the column. Some will be flushed out, and some will squeeze on top of the column. To solve this problem, a step gradient can be employed. By setting one of the steps to a field strength corresponding to the mobility of target protein, large amounts of protein can be held in the gradient with less distortion in gradient. At the same time, a broad range of proteins can still focus on the same column.

Electroosmotic flow (EOF) is generated by the charges present at the inner surface of the column or at the surface or interior of packing beads. In free solution, as in a capillary, electrophoresis gives rise to a bulk flow which strongly affects the shape and width of the solute bands. EOF increases the resolution of CE due to its uniform velocity profile in radial direction. In a packed column, the effects of a containing wall can be neglected if very small beads are used or the zeta potential of the wall is the same as the packing. By visualizing the packed column as parallel tubes with the potential of the wall being equal to that of the particles, EOF velocity profile is flat for the packed column. With this consideration, EOF might increase the resolution of DFGF. However, local EOF rates near focused protein bands may differ from the average and may cause distortion in the flow profile, which will degrade the separation.

When charged particles like silica gel were used as the packing, EOF, instead of the pump, is the main driving force to recirculate the coolant buffer. EOF works on very small beads, without generating high pressure. EOF is related to the zeta-potential, which depends on the charged state of the surface. One of the shortcomings of EOF pumping is that the zeta-potential can be easily influenced by factors such as temperature, alteration of the surface resulting from the adsorption of ions and molecules, and the concentration and pH of the buffer electrolytes. Ionic surfactants, such as CTAB, can provide significant change in the EOF rate, even reversing EOF and therefore might be used to adjust the flow rate for DFGF.

The dynamic electric field gradient focusing provided by the present invention relies on field gradient control, which includes hardware and software. Representative gradient control hardware and software are discussed below.

Figure 16:
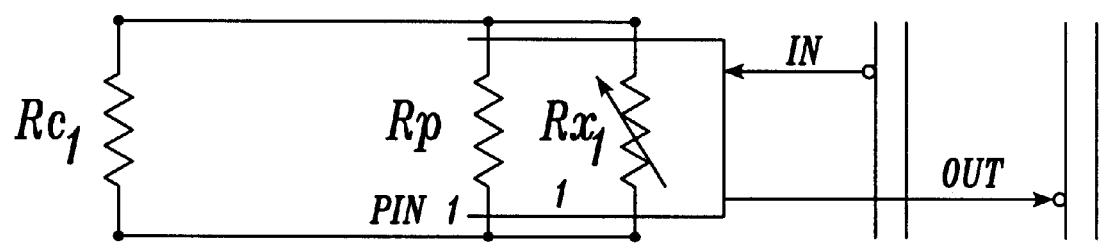
FIG. 16 is a schematic representation of the resistance between two adjacent electrodes in accordance with the present invention.
Figure 17:
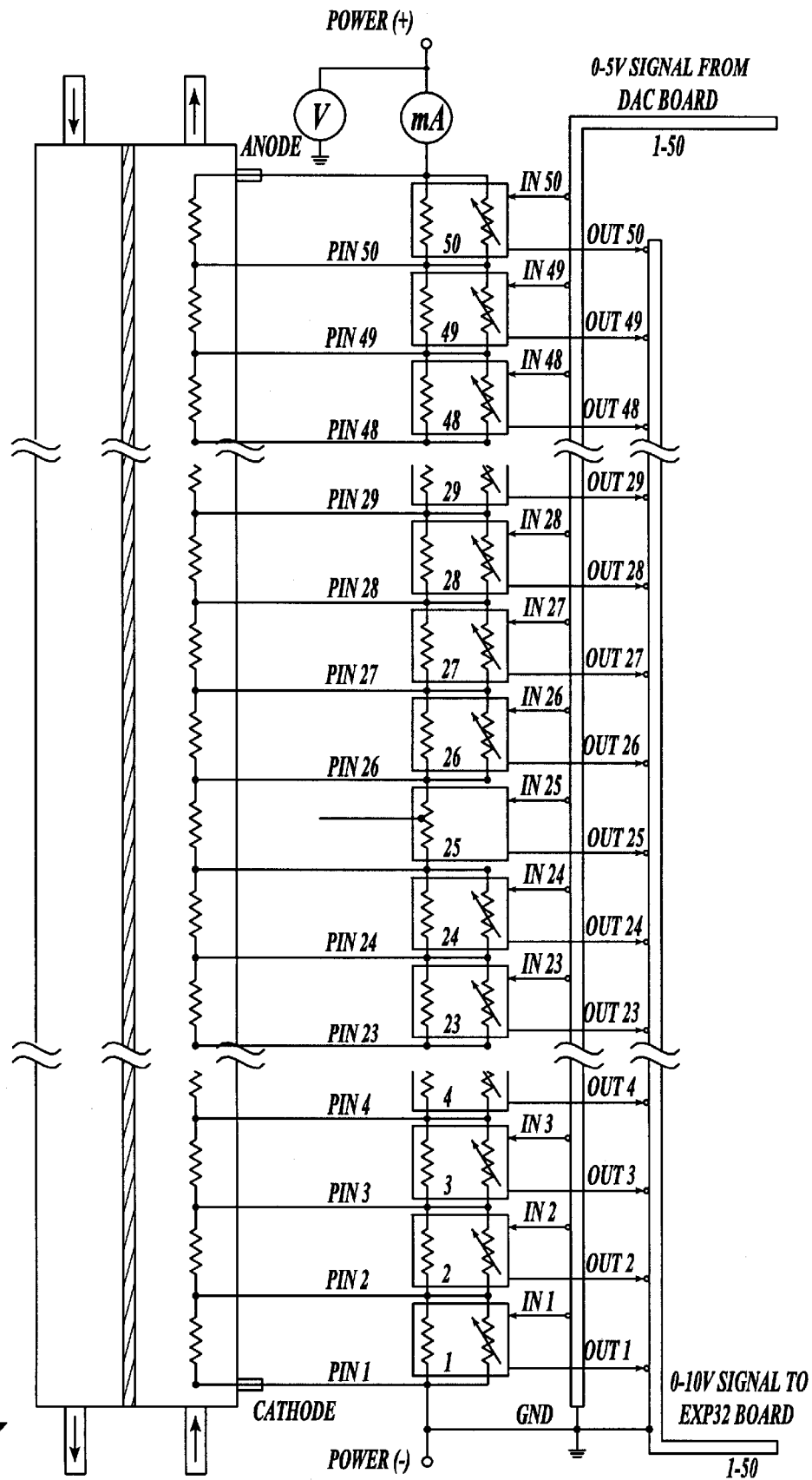
FIG. 17 is a schematic diagram of a representative electric field gradient focusing gradient control model, the blocks with dash line frame are controller units, each of the units handles the data acquisition and the resistance control adjacent two electrodes.

The control circuits are designed to manipulate the field gradient by adjusting the effective electrical resistance between each two adjacent electrodes (see FIG. 16). in one embodiment, each pair of electrodes is connected to one of the 50 controller units (FIG. 17).

The electrical resistance between two adjacent electrodes $R_i$ is determined by the sum of the resistance of three parallel resistors, $Rc_i$, $Rp_i$, and $Rx_i$. Note that the buffer between electrodes is considered as a resistor $Rc_i$.

$$R_i = \frac{Rc_i \cdot Rp_i \cdot Rx_i}{Rc_i \cdot Rp_i + Rc_i \cdot Rx_i + Rp_i \cdot Rx_i} \quad (12)$$

The resistors $Rp_i$ are used for protective purpose and have 1MΩ resistance. Because $R_p \gg Rc_i$, $R_p \gg Rx_1$. Equation (12) can be simplified as $$R_i = \frac{Rc_i \cdot Rx_i}{Rc_i + Rx_i} \quad (13)$$

By changing each $Rx_i$, the circuits adjust each $R_i$ indirectly. By Ohms Law, the potential drop between two electrodes is determined by the resistance between them if the total current going through is constant. The potential drop between the two adjacent electrodes is given by $$V_i = V_{total} \cdot \frac{R_i}{\sum_{i}^{50} R_i} \quad (14)$$

Since the field strength is proportional to the potential drop with the electrodes equally spaced, we can manipulate the field strength point by point by adjusting each $Rx_i$, independently.

$$E_i = \frac{V_i}{d} = \frac{V_{total}}{d} \frac{R_i}{\sum_{i}^{50} R_i} \quad (15)$$

where d is the distance between the two adjacent electrodes. An electric field gradient in any shape, linear or nonlinear, continuous or stepwise, can be produced with a limitation to the conductivity of the buffer. Note that the resistance between two parallel-connected resistors is always less than any one of them, in other words, $R_i < Rc_i$ must be satisfied.

There is more than one group of $R_i$ that satisfies Equation 15, in other words, different groups of $Rx_i$ can be used to establish the same field gradient with the total current going through the chamber arbitrarily. There is no unique equilibrium state. To solve the problem, a small modification to unit No. 25 is made by disabling its control function and replacing $Rp_{25}$ with a 5kΩ resistor. The total current going through the chamber was fixed, and given by $$I = \frac{V_{25} \cdot Rp_{25} \cdot Rc_{25}}{(Rp_{25} + Rc_{25})} \quad (16)$$

$V_{25}$ has a unique value for a specific field gradient, and can be calculated from the total potential drop across the chamber. $Rc_i$ is determined by the conductivity of the buffer. Therefore, there is a unique value of $Rx_i$ that satisfies Equation 15.

Figure 18:
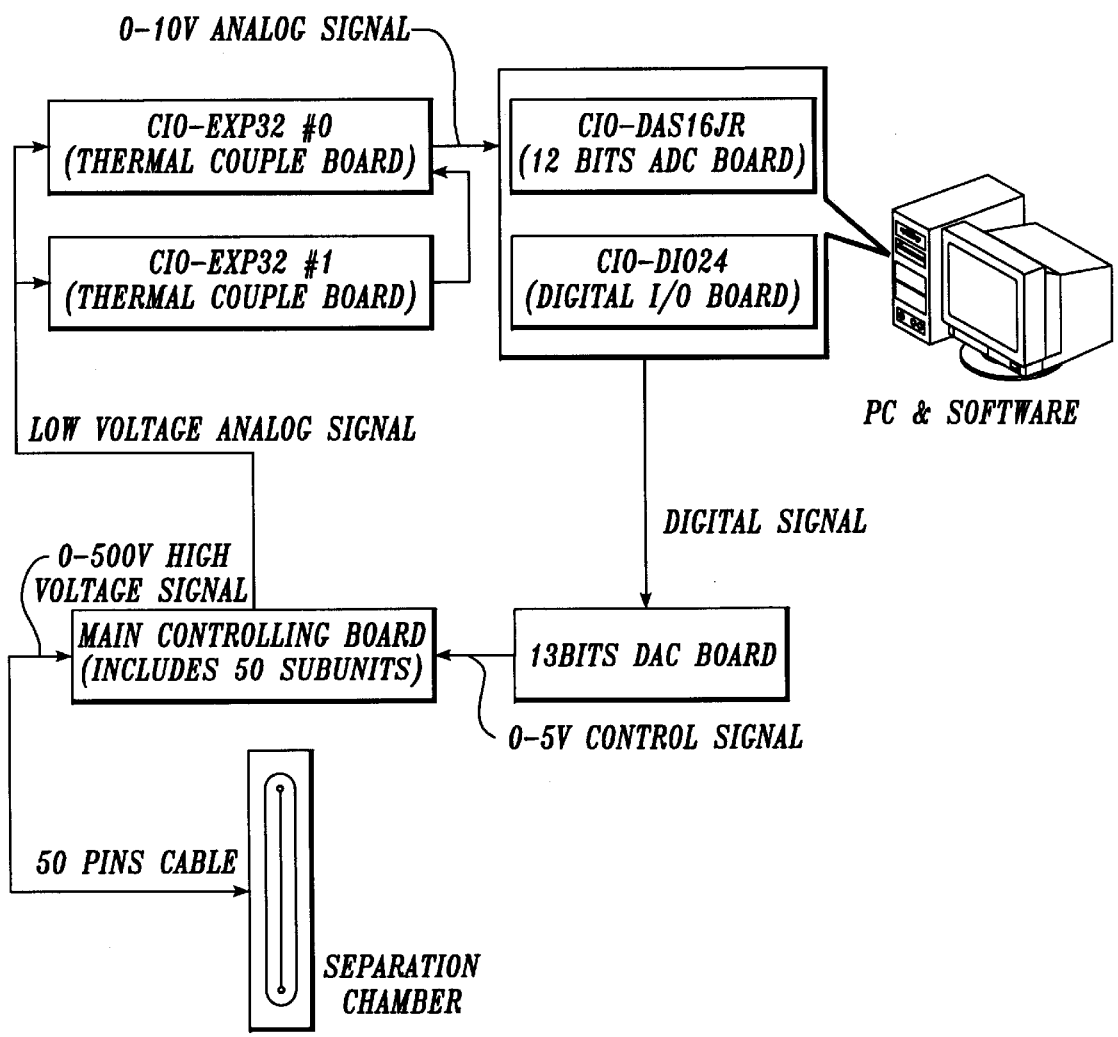
FIG. 18 is a schematic diagram of a representative electric field gradient focusing gradient control circuits, blocks represent electronic boards, the thick lines represent standard ribbon cables, data channels between the two CIO-EXP32 boards and the CIO-DAS16Jr board are programmed rather than being physically connected, CIO-DAS16Jr and CIO-DIO24 are plugged in extension slots of the PC.

Representative DFGF gradient control circuits are shown schematically in FIG. 18. Referring to FIG. 18, the PC monitor/controller board and the 13 bit DAC board were built in our laboratory. Some modifications have been made for better performance. The two thermocouple boards CIO-EXP32, the 16-channel ADC board CIO-DAS16/Jr and the 24-channel Digital I/O board CIO-DIO24 were purchased from ComputerBoards, Inc. Standard SCSI ribbon cables are used to connect all the boards. There are 50 controller units plugged into the mother board. Each unit corresponds to one pair of electrodes. The whole system was grounded to protect the circuits from unexpected shock.

Figure 19:
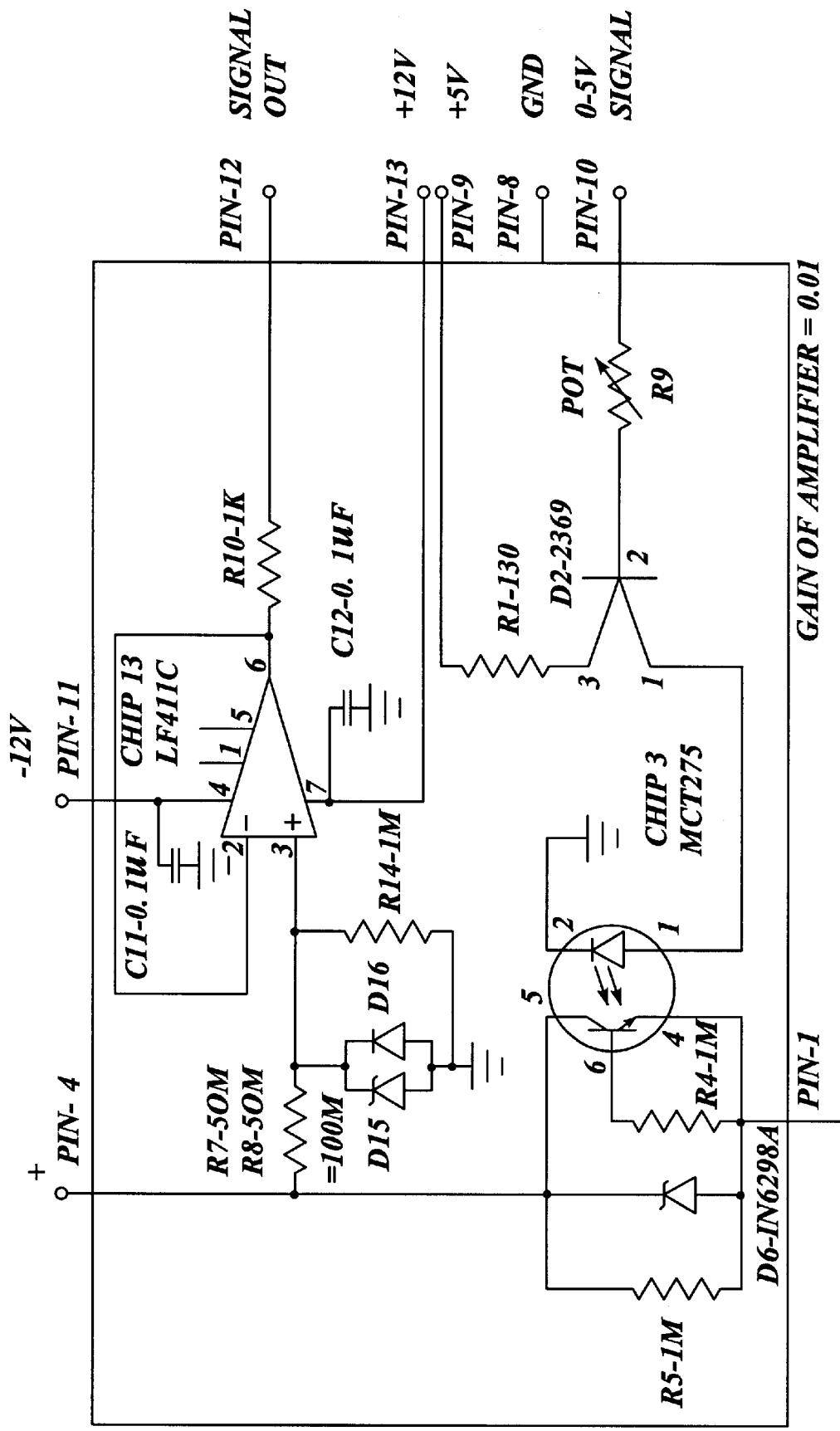
FIG. 19 is a circuit diagram of a representative controller unit, pin 1 and 4 were connected to electrodes and neighboring units, the electrical potential on the electrode is reduced by 1/100, then enters amplifier LF411C where the load of signal increased, the signal is then sent to EXP32 board through pin 12, the control signal (pin 10, 0–5 V) from the DAC board adjusts the current going through the optical isolator MCT275.
Figure 20:
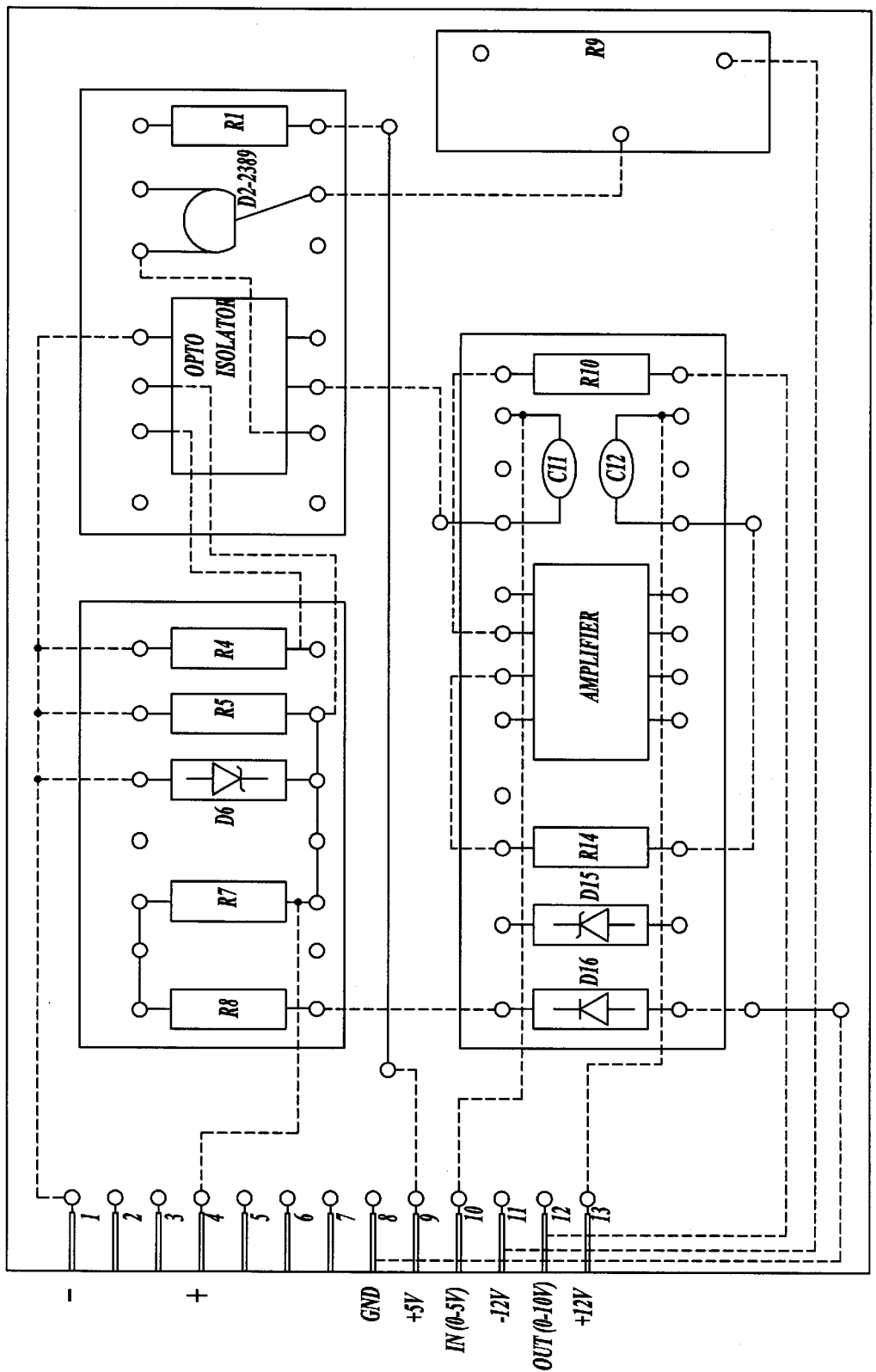
FIG. 20 is a circuit diagram of a representative controller unit.
Figure 21:
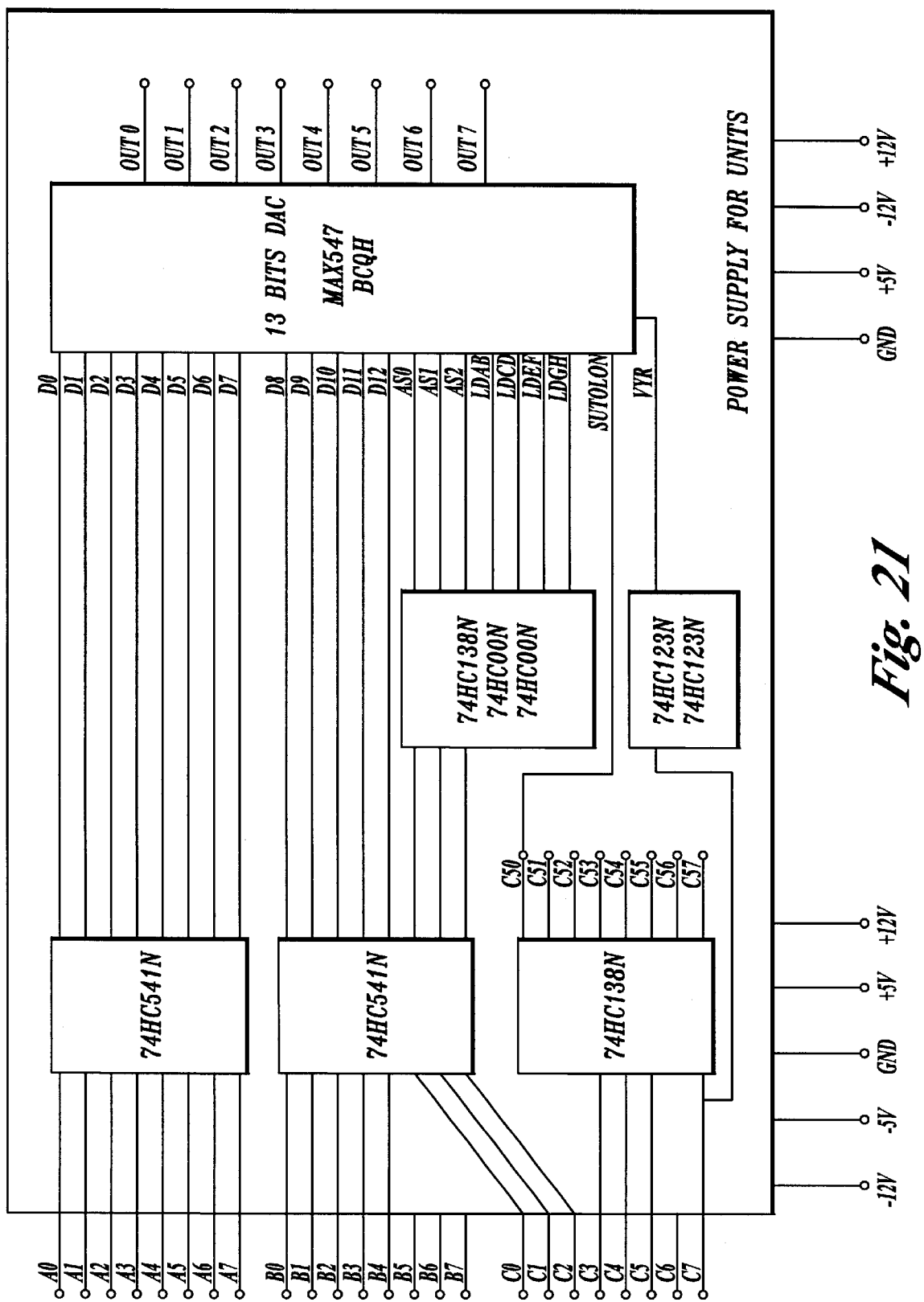
FIG. 21 is a schematic illustration of a representative DAC board circuit diagram illustrating connections.
Figure 22A:
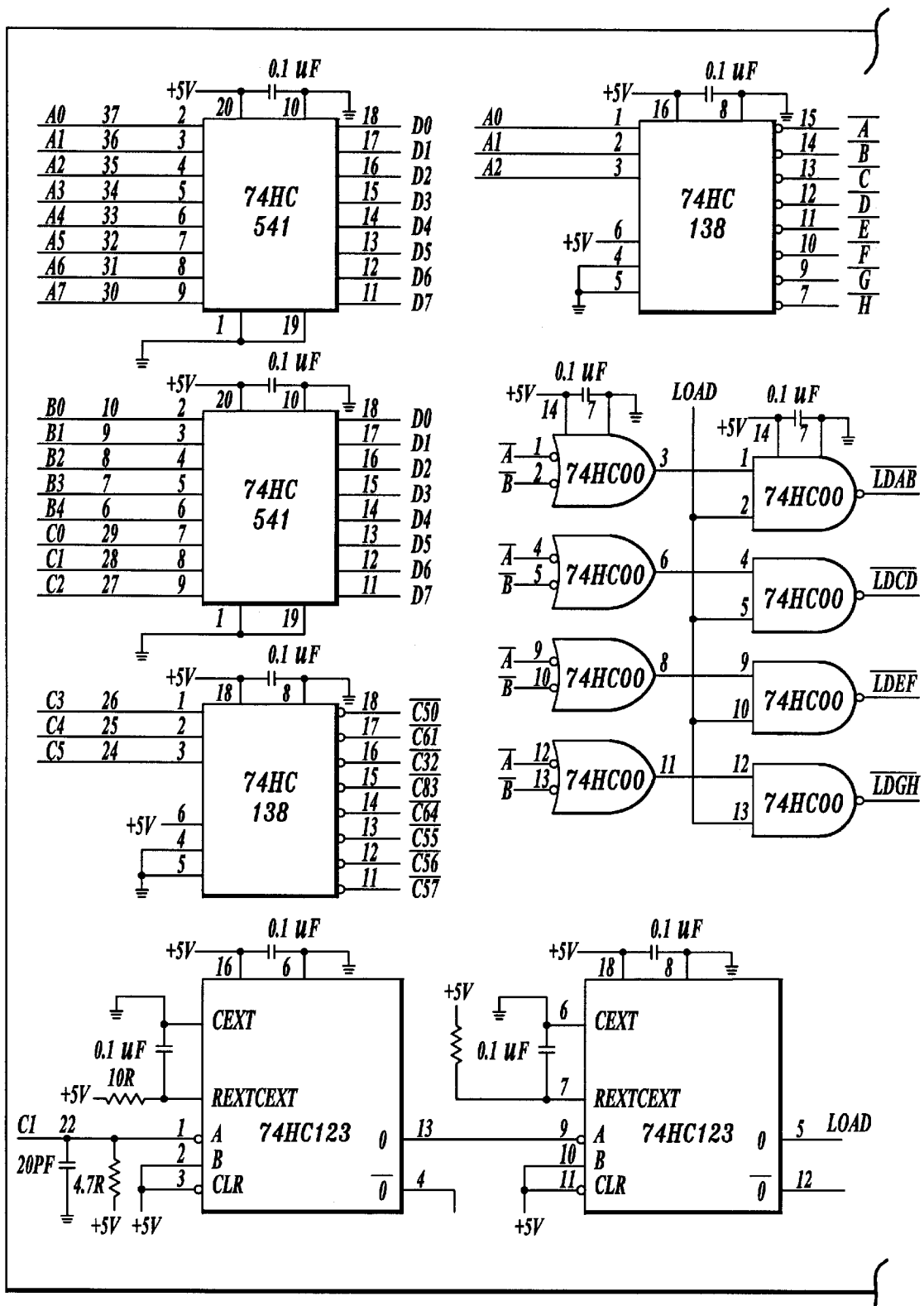
FIG. 22 is a schematic illustration of a representative DAC board circuit diagram illustrating components.
Figure 22B:
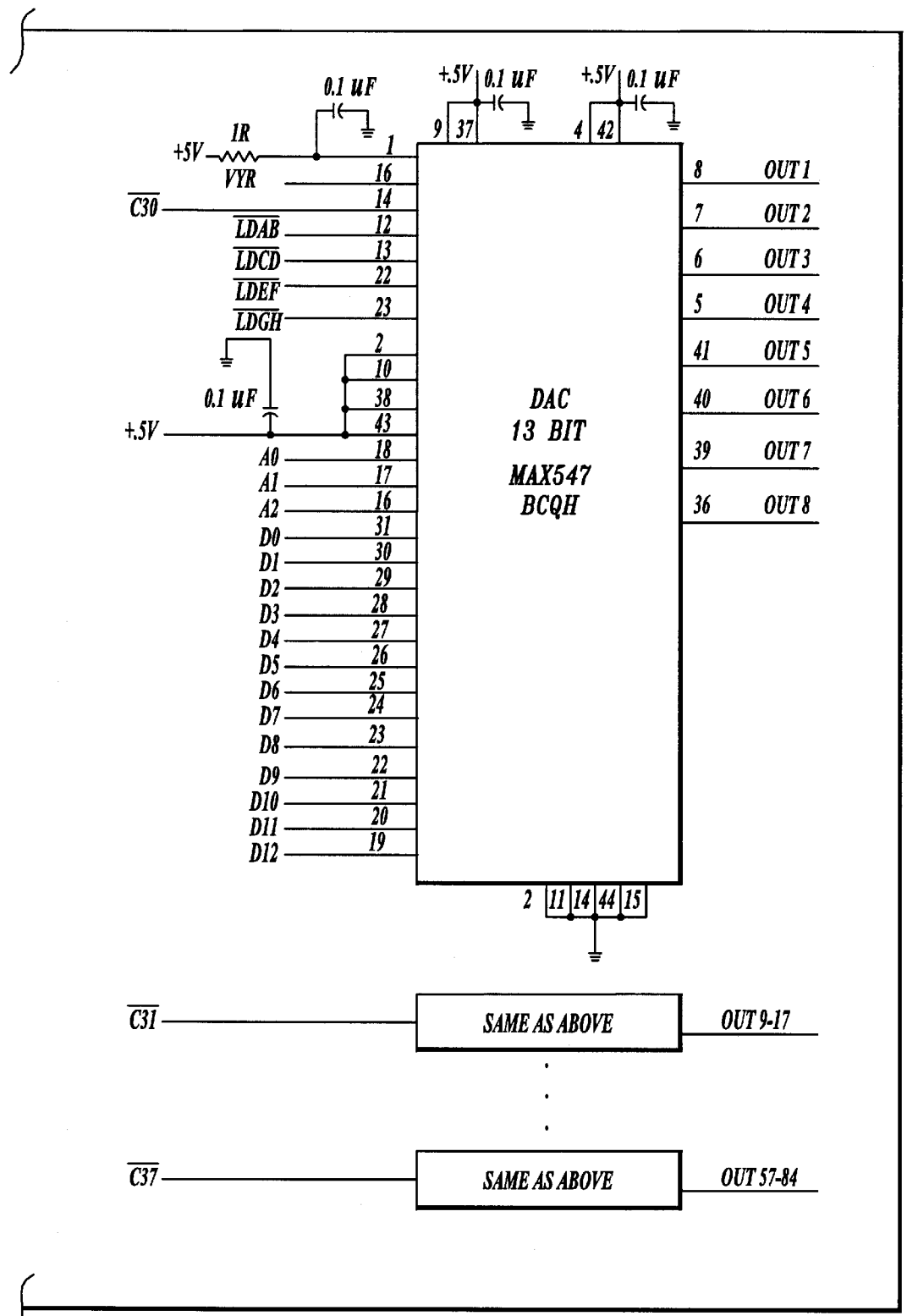

The gradient control is accomplished with PC-controlled circuits (see FIG. 19), which are composed of electronic circuit boards. A circuit diagram of the controller unit is shown in FIG. 20. A logic diagram for circuit diagram for ADC board is shown in FIG. 21. A circuit diagram for the ADC board with components identified is shown in FIG. 22.

The circuits scan all 50 electrodes and scale the signals down by 1/100. Then the signals were sent to ADC board where 0–10V analog signals are digitized. The computer compares these readings with the programmed gradient, then sends its commands in digital signals to DAC board via the Digital I/O boards. In the DAC board, the command signals are converted to 0–5V analog signals, then sent to the 50 units on the PC monitor/controller board. Those units adjust the current going through the units, or we can say change the values of resistance $Rx_i$. Note that the $Rx_i$ do not exist physically, and they are the resistance to current going through the chip MCT275, an optically isolated controller. The scan/response cycle for the circuits is set at about 0.5 sec, and could be adjusted by the program.

A 600V DC power supply (Xantrex) supplies power to the chamber. The power to all the boards is supplied by the computer.

A representative device of the invention was formed as described below and was used to: (1) focus a single protein from a dilute solution, and (2) fractionate a protein cocktail.

A representative separation chamber was built and assembled as described above. A 10×2 cm$^2$ dialysis membrane covered the trough to form a tube with a half round cross sectional area. The tube was packed with beads and serves as the separation chamber. On the other side of the membrane, a 3 mm thick TEFLON spacer with a 1 mm slot and a buffer chamber which was a trough machined on a piece of PLEXIGLAS plate, with 1 mm in width and 4 mm in depth, was arranged. The buffer chamber was a cuboid space through which the externally cooled electrolyte buffer flows. The recirculating buffer acts as coolant and electrolyte and removes electrolysis products from the electrodes.

A set of 50 platinum wires (0.25 mm OD) was sealed in a row of holes (0.05 inch between adjacent holes) in the plate with one side contacting the buffer and the other side connected to a 50 pin SMS-series micro strip (Samtec) which was mounted in a 2 mm deep slot machined on the outside of the plate. Through the strips, those electrodes were connected with external control circuits via a 50 pin standard SCSI ribbon cable.

A dialysis membrane (MWCO 6,000) between the packed column and buffer chamber allow ions to move in and out freely while the charged solutes (e.g., proteins and other macromolecules) in the column cannot penetrate the membrane. Furthermore, the dialysis membrane isolates the column from the electrodes to avoid disruption of the laminar flow by gas generation or denaturation of solute (e.g., protein) by contact with electrolysis products.

The column was packed from the top with a 125–150 μL/hr flow rate using the elution buffer. For charged packing materials, for example, silica gel, the bed was packed with a 500V reverse field.

Inlets for the elution buffer and coolant buffer were machined on the two PLEXIGLAS plates with corresponding interfaces installed. Additional ports designed for packing and unpacking were also machined at the end of the chamber.

The coolant buffer recirculates at a flow rate of about 50 L/hr between the separation chamber and a buffer reservoir in an ice-bath. A bubble trap was arranged in the coolant buffer route to prevent entrained gas bubbles from entering the separation chamber. A syringe pump was employed to push the elution buffer through the packed column at 15–150 μL/hr and to generate the convective flow that counteracts the electric field gradient. In the following examples, 10 mM Tris-Phosphate buffer was used for both the elution buffer and the recycle buffer. Protein sample was loaded onto the packed column through a 6-port sample injection valve which had a sample volume of 10 ul. All lines were PEEK with flangeless fittings.

Dialysis membrane was purchased from Scienceware® Bel-Art products with a 6,000 normal MWCO and 0.073 mm thickness. Particles of different sizes (see Table 3) and different materials (see Table 4) were been tested as packings for the separation column. Focusing of proteins was accomplished in all the packings tested. However, some packings provided good separation while others did not.

Generally, the smaller the particles, the higher the resolution. However, too small particles make it difficult to pump the buffer through the column. For charged particles, EOF can act as the pump. Excessive pressures can be avoided by using EOF pumping; however, an alternative way is required to control the flow rate, for example, by adjusting the viscosity of the buffer and the charge density on the surface of particles.

TABLE 3

Sizes of Symmetry Packings (Waters Corporation)

| Particles | Descriptions |
|---|---|
| Symmetry 3.5 um 100 A | 0.85 cc/gm pore volume; |
| Symmetry 5 μm 100 A | surface area = 335 m$^2$/g; |
| Symmetry 7 μm 100 A | 100 A average pore diameter; |
| Symmetry 12 μm 100 A (±25%) | Particle size distribution ± 18~20% of mean (volume) |
| Symmetry 5 μm 300 A | 0.75 cc/gm pore volume; surface area = 110 m$^2$/g; 275–300 A nominal pore diameter; Particle size distribution 5.5 μm ± 18~20% of mean (volume) |
| Nova-Pak Diol 4 μm 80 A | 0.25 cc/gm pore volume; surface area = 120 m$^2$/g; 80 A nominal pore diameter; acid treated to remove metals, but not high purity silica bonded to full coverage with Diol, no secondary end cap; Particle size distribution 4.5 μm ± 18% of mean (volume) |

TABLE 4

Materials Packing Beads

| Packing | Producer | Description |
|---|---|---|
| TOYOPEARL[1] 45 μm | TosoHAAS | HW-55F Size exclusion resin, resolution factor <1.2 Particle size: 30~60 μm Fractionation range (MW, globular): 1.000~700 × 10$^3$ |

TABLE 4-continued

Materials Packing Beads

| Packing | Producer | Description |
|---|---|---|
| SEC 10 μm[2] | Sigma | TSK G3000SW<br>Particle size: 10 μm<br>Fractionation range (MW, globular):<br>10~100 × 10³<br>Pore size: 250 A |
| Duke 5~60 μm | Duke Sci. Corp. | Glass microspheres<br>Duke Scientific Corporation<br>Particle size: 5~60 μm |
| Duke 5~38 μm | Duke Sci. Corp. | 5~38 fraction[3] of above particles<br>Particle size: 5~38 μm |
| 5 μm silica gel[3] | Sigma | HPLC sorbent<br>Particle size: 5 μm<br>Pore size: 60 A |
| Superose ® 12 | Sigma<br>Pharmacia LKB | Prep grade<br>Particle size: 20~40 μm<br>Fractionation range (MW, globular):<br>1000~300 × 10³ |

[1]TSKgel SW is a silica-based hydrophilic bonded phase for separations based on molecular size. Nonspecific interaction with proteins is minimal.
[2]TOYOPEARL HW: TOYOPEARL is totally porous, semirigid spherical gel designed for medium and low pressure liquid chromatography. TOYOPEARL HW gels are synthesized from hydrophilic vinyl polymer containing numerous hydroxyl groups and are composed exclusively of C, H and O atoms. TOYOPEARL HW is very strong mechanically and can be used at high flow rates.
[3]5~38 μm fraction was obtained by sieving the 5~60 μm with a 38 μm metal screen.
[4]Silica gel for normal phase adsorption-partition chromatography.

Before loading a sample, the packed column was cleaned with 0.1 M NaOH and 10% Tween-20, and equilibrated with elution buffer for at least 30 minutes. The coolant buffer in the reservoir was brought to the operating temperature (below 8° C.). A 10 μL protein sample was injected into the column and, before it reached the outlet, the controller was booted using a default voltage pattern and the power supply was set at 150–500 V.

A global electric field gradient was selected from the keyboard. The computer program adjusted the electrode voltages gradually until this gradient was attained. Typically, an electric field gradient reaches its equilibrium state within five minutes. The protein sample focused as bands in 30 minutes and kept changing its shape until equilibrium was reached. The pumping rate of elution buffer and the gradient setting were adjusted to improve resolution. Usually, colored proteins were used as samples and the shape and position of the bands were recorded with a camera or camcorder.

The first group of experiments was the focusing of a single protein sample from a dilute solution to a band of more concentrated protein to demonstrate that DFGF is capable of focusing proteins in an electric field gradient.

The second experiment demonstrates the purification potential and resolving power of DFGF by fractionating a protein cocktail into isolated bands.

All the experiments were performed in a 10 mM Tris-phosphate buffer because the buffer system has low conductivity and still has a considerable buffer capacity. A low conductivity buffer is preferred for DFGF. Another advantage of low conductivity buffer is that a field gradient can be maintained more readily than in a high conductivity buffer system.

Figure 23:
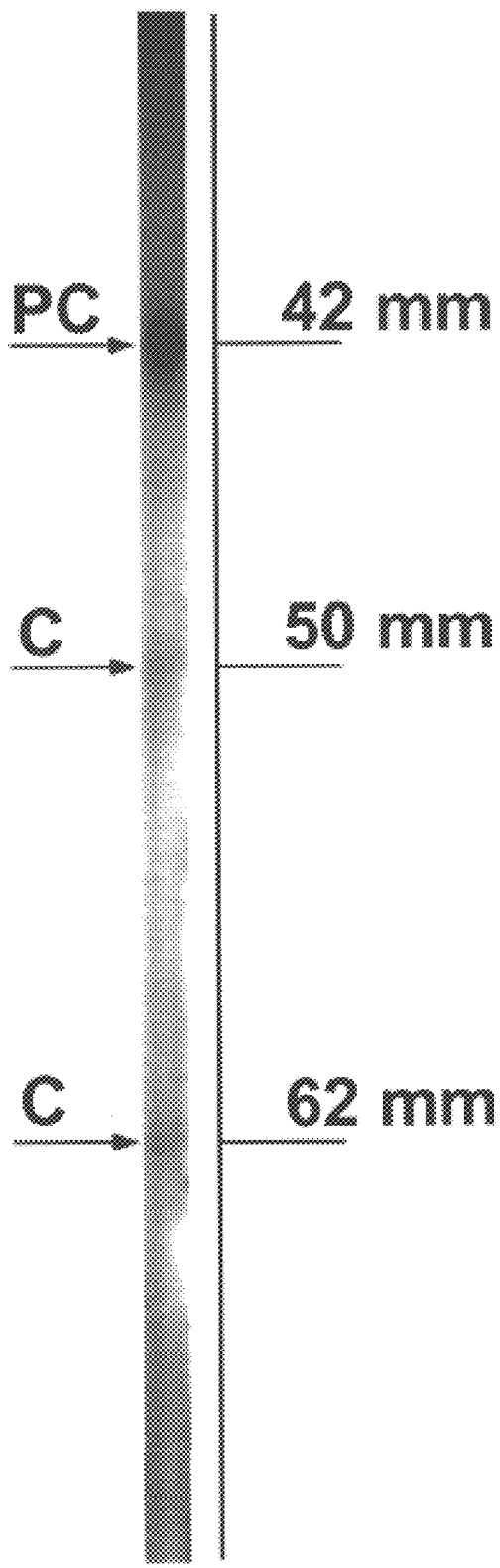
FIG. 23 is a digitized image of R-phycocyanin (PC) and two contaminants (C) focused in accordance with the present invention.

A sample of 0.5 mg/mL R-Phycocyanin (Sigma P-1536) was focused at a flow rate of 40 μL/hr and a linear gradient of 9.3 V/cm². The total voltage applied was 300 V, and a total current 3.409 mA. The picture taken 2.5 hours after power-on shows that the sample focused as three separated bands (FIG. 23). A vivid blue-green main band (1 mm height, 42 mm from top inlet), a faint blue band (2 mm height, 50 mm from inlet) and a faint gray band (2 mm height, 62 mm from inlet) were observed. The last two bands are contaminants in the sample.

To demonstrate the purification potential of DFGF, a model protein mixture (or "cocktail") was loaded onto the column. The four-in-one cocktail proteins (0.28 mg/ml R-Phycoerythrin (PE), 0.33 mg/ml Carbonic anhydrase conjugate (CAC), 0.25 mg/ml R-Phycocyanin (PC), 0.5 mg/ml Myoglobin, Sigma) were focused as separate bands in the column (see FIG. 24). Focusing was accomplished with a linear gradient of 13.0 v/cm² and a flow rate of about 18 μl/hr. 300 V was applied across the chamber; the current was 3.245 mA.

In all of the experiments above, focusing was carried out in 10 mM Tris-phosphate buffer at pH 7.0 (25° C.). Nova-Pak Diol silica gel beads with 4 μm nominal particle size and 80 A nominal pore size (Waters) was used for the packed column.

The resolution of the technique can be estimated from the minimum difference in properties that allows isolation of two adjacent bands. By measuring the distance between the two adjacent bands in the packed column, a sample calculation can be used to determine the difference in electromobility of two components.

For example, in the separation of the protein cocktail (FIG. 24), the distance between the two minor bands of R-Phycocyanin is 1 mm, the difference in field strength between the positions of the two bands is about 1.3 V/cm and the average field strength is 34.6 V/cm. The relative difference in electromobility between the two bands is estimated to be about 3.8%.

In another experiment, two 0.2 mm height myoglobin (Sigma M-1882) bands were observed focused in a 21.7 V/cm² linear gradient with 0.5 mm between them. Similarly, the resolution was estimated to be about 1.3% different in electromobility.

Compared with some available electrophoresis techniques, for instance SDS-PAGE, which can routinely isolate a discrete spectrum of proteins whose molecular weights differ by less than 2%, the resolving power of DFGF is very competitive.

TABLE 5

Electromobility of Protein Samples

| Protein Sample | Superficial Flow Rate (μl/hr) | Field Gradient (V/cm²) | Bands Position (mm) |
|---|---|---|---|
| CAD[1] | 40.0 | 9.3 | 28.5 |
| PE | 44.0 | 13.0 | 40.0 |
| Ferritin | 39.0 | 3.7 | 34.5 |
|  |  |  | 42.0 |
| PC[2] | 42.0 | 13.0 | 55.0 |
|  |  |  | 57.0 |
| Myoglobin[3] | 37.5 | 3.7 | 17.0 |
|  |  |  | 20.0 |

[1]Dye-labeled carbonic anhydrase by conjugating Carbonic anhydrase (Sigma) with Texas Red - X (Molecular Probes FluoReporter ®).
[2]At this condition only two bands of R-Phycocyanin were observed.
[3]The mobility data of myoglobin (Sigma, M-9267) was obtained in 10 mM Tris-phosphate buffer at pH 8.0.

Figure 24:
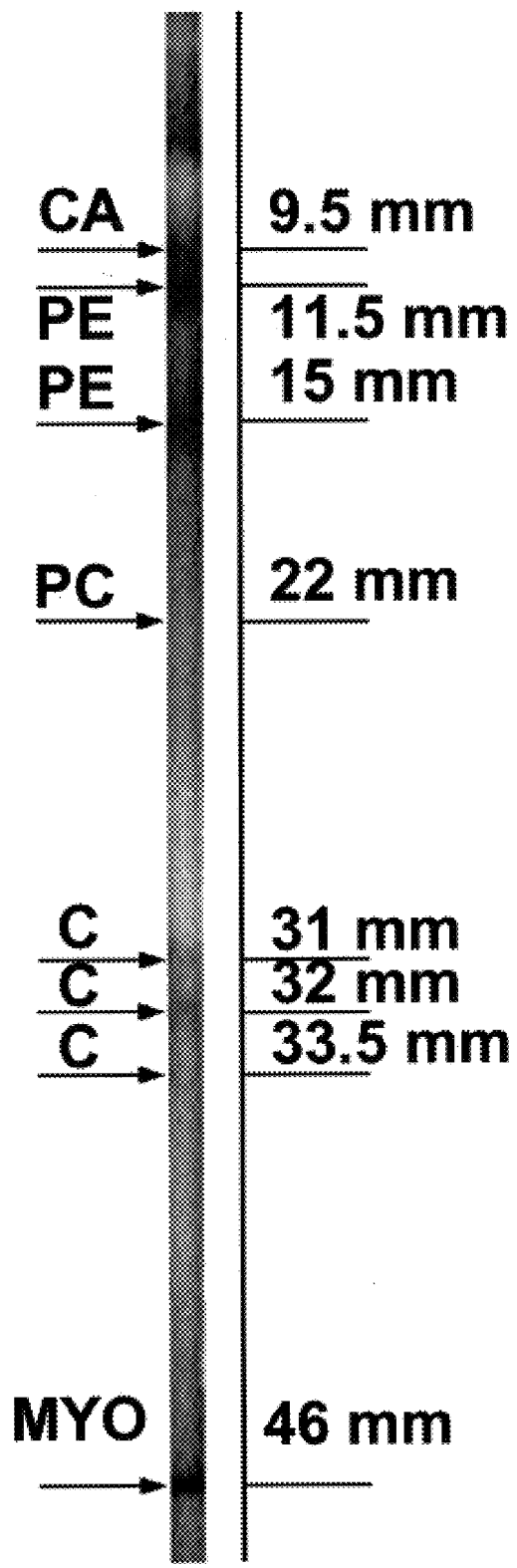
FIG. 24 is a digitized image of CA, PE, PC, CA, MYO, and contaminants (C) focused in accordance with present invention.

The average protein concentration in the focused bands can be estimated from the height of the band. For example, the myoglobin band in FIG. 24 is about 0.5 mm in height, the volume occupied by the focused band can be calculated from the cross sectional area of the column. The myoglobin in the sample was concentrated by 37 fold, from 10 µl, to 0.27 µL. The average concentration in the band was about 18.5 mg/ml. Subtracting the volume of the packing, protein concentrations as high as 50 mg/ml can be obtained in focused bands in DFGF column.

For most proteins, the solubility is lowest in the buffer with pH equal to its pI. DFGF is generally carried out in a buffer with pH differing from the isoelectric point (pI) of the target proteins. For this reason, DFGF can provide highly concentrated protein bands in a low ionic strength buffer without precipitation.

Figure 25A:
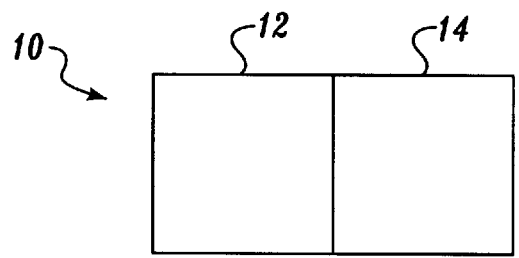
FIG. 25 is a schematic illustration of representative configurations for the device formed in accordance with the present invention.
Figure 25B:
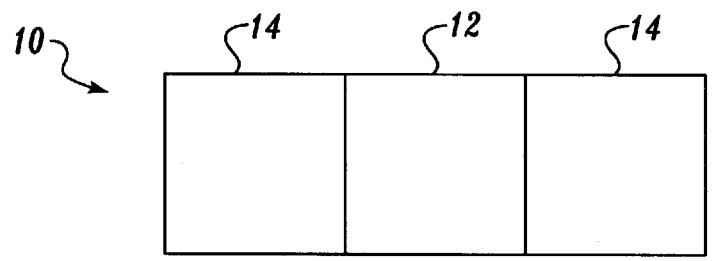
Figure 25C:
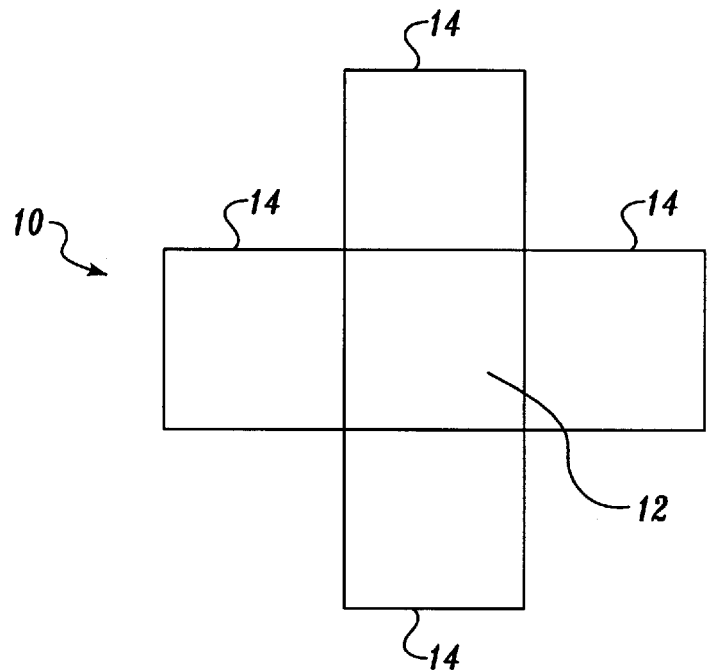

The device of the present invention includes a focusing chamber. As noted above, the focusing chamber can include more than one electrode array. For example, two electrode arrays can be associated with a single separation chamber in a configuration in which the separation chamber is positioned in between the two arrays. Similarly, the focusing chamber can include, for example, four arrays positioned about a separation chamber in a quadrupole-type configuration. Representative devices including one, two, and four electrode arrays are illustrated schematically in FIGS. 25A–C. Referring to FIG. 25, representative device 10 including a single electrode array (i.e., electrode chamber 14) and a separation chamber (i.e., chamber 12) is shown in FIG. 25A. FIGS. 25B and 25C illustrate representative devices having two and four electrode arrays arranged about a separation chamber.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A device for focusing a charged solute comprising:
   a first chamber for receiving a fluid medium, the first chamber having an inlet for introducing a first liquid to the chamber and an outlet for exiting the first liquid from the chamber;
   a second chamber comprising an electrode array, the second chamber having an inlet for introducing a second liquid to the chamber and an outlet for exiting the second liquid from the chamber; and
   a porous material separating the first and second chambers;
   wherein the electrode array comprises a plurality of electrodes arranged linearly along the chamber length, and wherein the electrodes are pin-shaped.

2. A device for focusing a charged solute comprising:
   a first chamber for receiving a fluid medium, the first chamber having an inlet for introducing a first liquid to the chamber and an outlet for exiting the first liquid from the chamber;
   a second chamber comprising an electrode array, the second chamber having an inlet for introducing a second liquid to the chamber and an outlet for exiting the second liquid from the chamber; and
   a porous material separating the first and second chambers;
   wherein the electrode array comprises a plurality of electrodes arranged linearly along the chamber length, and wherein the electrodes are staple-shaped.

3. A device for focusing a charged solute comprising:
   a first chamber for receiving a fluid medium, the first chamber having an inlet for introducing a first liquid to the chamber and an outlet for exiting the first liquid from the chamber;
   a second chamber comprising an electrode array, the second chamber having an inlet for introducing a second liquid to the chamber and an outlet for exiting the second liquid from the chamber; and
   a porous material separating the first and second chambers;
   wherein the electrode array comprises an electrode array positioned on a surface of the second chamber opposing the porous material.

4. A device for focusing a charged solute comprising:
   a first chamber for receiving a fluid medium, the first chamber having an inlet for introducing a first liquid to the chamber and an outlet for exiting the first liquid from the chamber;
   a second chamber comprising an electrode array, the second chamber having an inlet for introducing a second liquid to the chamber and an outlet for exiting the second liquid from the chamber; and
   a porous material separating the first and second chambers;
   wherein the electrode array comprises a first electrode array and a second electrode array, the first and second arrays positioned on opposing surfaces of the second chamber adjacent the porous material.

5. A device for focusing a charged solute comprising:
   a first chamber for receiving a fluid medium, the first chamber having an inlet for introducing a first liquid to the chamber and an outlet for exiting the first liquid from the chamber;
   a second chamber comprising an electrode array, the second chamber having an inlet for introducing a second liquid to the chamber and an outlet for exiting the second liquid from the chamber; and
   a porous material separating the first and second chambers;
   wherein the fluid medium comprises a chromatography support material.

6. A device for focusing a charged solute comprising:
   a first chamber for receiving a fluid medium, the first chamber having an inlet for introducing a first liquid to the chamber and an outlet for exiting the first liquid from the chamber;
   a second chamber comprising an electrode array, the second chamber having an inlet for introducing a second liquid to the chamber and an outlet for exiting the second liquid from the chamber; and
   a porous material separating the first and second chambers;
   wherein the second chamber further comprises an electrode pair, wherein the electrodes of the pair are positioned adjacent opposing ends of the electrode array.

7. A device for focusing a charged solute comprising:
   a first block having a first trough machined therein for receiving a fluid medium, the first trough having an inlet for introducing a first liquid to the trough and an outlet for exiting the first liquid from the trough;
   a second block having a second trough machined therein, wherein the second block comprises a electrode array positioned in the trough, the second trough having an inlet for introducing a second liquid to the trough and an outlet for exiting the second liquid from the trough, wherein the first trough and the second trough are substantially coincident and form a channel when the first block is sealed to the second block; and a porous material intermediate the first and second blocks, wherein the porous material divides the channel formed when the first block is sealed to the second block into a first chamber and a second chamber, the second chamber including the electrode array.

8. The device of claim 7 wherein the first and second chambers are in liquid communication when the chambers are filled with liquid.

9. The device of claim 7 wherein the first chamber is in electrical communication with the electrode array when the chambers are filled with a conductive liquid.

10. The device of claim 7 wherein the electrode array comprises a plurality of electrodes arranged linearly along the chamber length.

11. The device of claim 10 further comprising a voltage controller for controlling the voltage applied to each electrode of the electrode array.

12. The device of claim 11 wherein the voltage applied to each electrode of the electrode array generates an electric field gradient profile.

13. The device of claim 12 wherein the voltage controller dynamically controls the electric field gradient profile.

14. The device of claim 10 wherein the electrodes are pin-shaped.

15. The device of claim 10 wherein the electrodes are staple-shaped.

16. The device of claim 7 wherein the electrode array comprises an electrode array positioned on a surface of the second chamber opposing the porous material.

17. The device of claim 7 wherein the electrode array comprises a first electrode array and a second electrode array, the first and second arrays positioned on opposing surfaces of the second chamber adjacent the porous material.

18. The device of claim 7 wherein the fluid medium comprises a chromatography support material.

19. The device of claim 7 wherein the fluid medium comprises a polymer solution.

20. The device of claim 7 wherein the second chamber further comprises an electrode pair, wherein the electrodes of the pair are positioned adjacent opposing ends of the electrode array.

21. The device of claim 7 further comprising a first conduit for introducing the first liquid into the first chamber and a second conduit for exiting the first liquid from the first chamber.

22. The device of claim 7 wherein the first block is sealed to the second block through bolts passing through the blocks.

23. The device of claim 7 further comprising a resilient sheet intermediate the second block and the porous material, wherein the sheet has an aperture coincident with the first and second troughs when the sheet is positioned intermediate the blocks.

24. The device of claim 7 further comprising a sealant intermediate the second block and the resilient sheet.

25. A method for focusing a charged solute using the device of claim 7, wherein the charged solute comprises a biological solute selected from the group consisting of a protein, peptide, oligonucleotide, polynucleotide, and mixtures thereof.

26. A method for focusing a charged solute in a fluid medium comprising:
   introducing a charged solute into a fluid medium; and
   applying an electric field gradient to the charged solute in the fluid medium to cause the charged solute to focus in a region of the medium, wherein the electric field gradient is generated by an electrode array, wherein the electric field gradient is dynamically controlled.

27. A method for focusing a charged solute in a fluid medium comprising:
   introducing a charged solute into a fluid medium; and
   applying an electric field gradient to the charged solute in the fluid medium to cause the charged solute to focus in a region of the medium, wherein the electric field gradient is generated by an electrode array, wherein the electric field gradient is changed during the course of focusing the charged solute.

28. A method for focusing a charged solute in a fluid medium comprising:
   introducing a charged solute into a fluid medium; and
   applying an electric field gradient to the charged solute in the fluid medium to cause the charged solute to focus in a region of the medium, wherein the electric field gradient is generated by an electrode array, wherein the fluid medium comprises a chromatography support material.

29. A method for focusing a charged solute in a fluid medium comprising:
   introducing a charged solute into a fluid medium; and
   applying an electric field gradient to the charged solute in the fluid medium to cause the charged solute to focus in a region of the medium, wherein the electric field gradient is generated by an electrode array, wherein the fluid medium comprises a polymer solution.

30. A method for focusing a charged solute in a fluid medium comprising:
   introducing a charged solute into a fluid medium; and
   applying an electric field gradient to the charged solute in the fluid medium to cause the charged solute to focus in a region of the medium, wherein the electric field gradient is generated by an electrode array, wherein the charged solute comprises an uncharged material sorbed into a charged carrier.

31. A method for focusing a charged solute in a fluid medium comprising:
   introducing, a charged solute into a fluid medium; and
   applying an electric field gradient to the charged solute in the fluid medium to cause the charged solute to focus in a region of the medium, wherein the electric field gradient is generated by an electrode array, wherein the electrode array comprises a plurality of electrodes arranged linearly along an axis parallel to direction of migration of the charged solute in the fluid medium, and wherein each electrode is individually controlled.

32. A method for focusing a charged solute in a fluid medium comprising:
   introducing a charged solute into a fluid medium, wherein the fluid medium is contained in a device comprising
   a first block having a first trough machined therein for receiving a fluid medium, the first trough having an inlet for introducing a first liquid to the trough and an outlet for exiting the first liquid from the trough;
   a second block having a second trough machined therein, wherein the second block comprises an electrode array positioned in the trough, the second trough having an inlet for introducing a second liquid to the trough and an outlet for exiting substantially coincident and form a channel when the first block is sealed to the second block; and
   a porous material intermediate the first and second blocks, wherein the porous material divides the channel formed when the first block is sealed to the second block into a first chamber and a second chamber, the second chamber including the electrode array; and applying an electric field gradient to the charged solute in the fluid medium to cause the charged solute to focus in a region of the medium.

33. The method of claim 32 wherein the first liquid is an eluant buffer.

34. The method of claim 32 wherein the second liquid is a coolant buffer.

35. The method of claim 32 wherein the first liquid is the same as the second liquid.

36. The method of claim 32 wherein the first liquid is different from the second liquid.

37. A method for focusing a charged solute comprising:
applying a charged solute to a fluid medium;
applying a hydrodynamic force to the solute in the fluid medium; and
opposing the hydrodynamic force with an electric field gradient to provide a solute focused in the fluid medium, wherein the electric field gradient is generated by an electrode array, wherein the electrode array comprises a plurality of electrodes arranged linearly along an axis parallel to direction of migration of the charged solute in the fluid medium, and wherein each electrode is individually controlled.

38. A method for focusing a charged solute comprising:
applying a charged solute to a fluid medium;
applying a hydrodynamic force to the solute in the fluid medium; and
opposing the hydrodynamic force with an electric field gradient to provide a solute focused in the fluid medium, wherein the electric field gradient is generated by an electrode array, wherein the electric field gradient is dynamically controlled.

39. A method for focusing a charged solute comprising:
applying a charged solute to a fluid medium;
applying a hydrodynamic force to the solute in the fluid medium; and
opposing the hydrodynamic force with an electric field gradient to provide a solute focused in the fluid medium, wherein the electric field gradient is generated by an electrode array, wherein the electric field gradient is changed during the course of focusing the charged solute.

40. A method for focusing a charged solute comprising:
applying a charged solute to a fluid medium;
applying a hydrodynamic force to the solute in the fluid medium; and
opposing the hydrodynamic force with an electric field gradient to provide a solute focused in the fluid medium, wherein the electric field gradient is generated by an electrode array, wherein the fluid medium comprises a chromatography support material.

41. A method for separating charged solutes comprising:
applying a mixture of charged solutes to a fluid medium;
applying a hydrodynamic force to the solutes in the fluid medium; and
opposing the hydrodynamic force with an electric field gradient to separate the charged solutes in order of their electrophoretic mobilities, wherein the electric field gradient is generated by an electrode array, wherein each electrode is individually controlled.

42. A method for separating charged solutes comprising:
applying a mixture of charged solutes to a fluid medium:
applying a hydrodynamic force to the solutes in the fluid medium; and
opposing the hydrodynamic force with an electric field gradient to separate the charged solutes in order of their electrophoretic mobilities, wherein the electric field gradient is generated by an electrode array wherein the electric field gradient is dynamically controlled.

43. A method for separating charged solutes comprising:
applying a mixture of charged solutes to a fluid medium;
applying a hydrodynamic force to the solutes in the fluid medium; and
opposing the hydrodynamic force with an electric field gradient to separate the charged solutes in order of their electrophoretic mobilities, wherein the electric field gradient is generated by an electrode array, wherein the electric field gradient is changed during the course of separating the charged solute.

44. A method for separating charged solutes comprising:
applying a mixture of charged solutes to a fluid medium;
applying a hydrodynamic force to the solutes in the fluid medium; and
opposing the hydrodynamic force with an electric field gradient to separate the charged solutes in order of their electrophoretic mobilities, wherein the electric field gradient is generated by an electrode array, wherein the fluid medium comprises a chromatography support material.

* * * * *

UNITED STATES PATENT AND TRADEMARK OFFICE
CERTIFICATE OF CORRECTION

PATENT NO. : 6,277,258 B1
DATED : August 21, 2001
INVENTOR(S) : C.F. Ivory et al.

It is certified that error appears in the above-identified patent and that said Letters Patent is hereby corrected as shown below:

Title page,
Item [56], References Cited, OTHER PUBLICATIONS, delete this reference:
"W.S. Koegler et al, "Field Gradient Focusing: A Novel Method for Protein Separation", Journal of the American Chemical Society and American Institute of Chemical Engineers, 15 pages, 1996*."

Column 1,
Line 11, after "by reference." insert a new paragraph -- This invention was made with government support under DES-9417239 awarded by the National Science Foundation. The government has certain rights in the invention. --
Line 15, "particularly" should read -- particularly, --
Line 37, "*Purif*" should read -- *Purif.* --

Column 2,
Line 22, "Biotechnol" should read -- Biotechnol. --

Column 4,
Line 54, after "load of signal" insert -- is --

Column 5,
Line 24, "pls," should read -- pIs, --
Line 32, ":includes" should read -- includes --
Line 52, "electrode's" should read -- electrodes --

Column 7,
Line 60, "blocks 1 10" should read -- blocks 110 --

Column 8,
Line 55, "FIG. 6A" should read -- FIGS. 6A --

Column 10,
Line 5, "controllers" should read -- controllers' --
Lines 27-28, the paragraph that starts at line 28, beginning with the words "Tosohaus. Various. . ." should be a continuation of the previous paragraph Column 12,
Line 40, "a," should read -- $\sigma$, --
Line 45, "$I_X=I_{O,x}+xI_{1,x}$" should read -- $I_X=I_{0,x}+xI_{1,x}$ --
Line 59, "X," should read -- $x$, --

UNITED STATES PATENT AND TRADEMARK OFFICE
CERTIFICATE OF CORRECTION

PATENT NO. : 6,277,258 B1
DATED : August 21, 2001
INVENTOR(S) : C.F. Ivory et al.

It is certified that error appears in the above-identified patent and that said Letters Patent is hereby corrected as shown below:

Column 13,
Line 40, Table 2, line 1 of data, "$cm^2$/V-s" should read -- $cm^2$/V•s --
Line 41, Table 2, line 2 of data, "$cm^2$/V-s" should read -- $cm^2$/V•s --
Line 42, Table 2, line 3 of data, "$cm^2$/V-s" should read -- $cm^2$/V•s --
Line 43, Table 2, line 4 of data "$cm^2$/V-s" should read -- $cm^2$/V•s --
Line 44, Table 2, line 5 of data "$cm^2$/V-s" should read -- $cm^2$/V•s --
Line 55, "proteins" should read -- proteins' --

Column 14,
Line 32, "elbctrophoresis," should read -- Electrophoresis, --
Line 65, "diff-use" should read -- diffuse --

Column 15,
Line 30, after "must have" insert -- an --

Column 16,
Line 46, after "instability" insert -- . --
Line 47, "IN" should read -- IN --.

Column 17,
Line 16, "*J Chromatography*, 1996 229:p. 229-236," should read -- *J. Chromatography*, 1996 229:229-236, --

Column 19,
Line 36, "half round" should read -- half-round --

Column 20,
Line 21, "were been" should read -- were being --
Line 39, Table 3, line 1 of data "3.5 um" should read -- 3.5 $\mu$m --

Column 24,
Line 61, "a electrode" should read -- an electrode --

UNITED STATES PATENT AND TRADEMARK OFFICE
CERTIFICATE OF CORRECTION

PATENT NO.   : 6,277,258 B1
DATED        : August 21, 2001
INVENTOR(S)  : C.F. Ivory et al.

It is certified that error appears in the above-identified patent and that said Letters Patent is hereby corrected as shown below:

<u>Column 26,</u>
Line 38, after "introducing" delete ","
Line 50, after "comprising" insert -- : --
Line 59, before "substantially coincident" insert -- the second liquid from the trough, wherein the first trough and the second trough are --

Signed and Sealed this

Twenty-seventh Day of August, 2002

*Attest:*

*Attesting Officer*

JAMES E. ROGAN
*Director of the United States Patent and Trademark Office*